(12) United States Patent
Wlaschin et al.

(10) Patent No.: US 8,460,689 B2
(45) Date of Patent: Jun. 11, 2013

(54) ORAL CARE METHOD AND KIT

(75) Inventors: Katie F. Wlaschin, St. Paul, MN (US); Alan R. Dombrowski, Woodbury, MN (US); Matthew T. Scholz, Woodbury, MN (US); Ranjani V. Parthasarathy, Woodbury, MN (US)

(73) Assignee: 3M Innovative Properties Company, St Paul, MN (US)

( * ) Notice: Subject to any disclaimer, the term of this patent is extended or adjusted under 35 U.S.C. 154(b) by 132 days.

(21) Appl. No.: 12/775,197

(22) Filed: May 6, 2010

(65) Prior Publication Data

US 2010/0285148 A1    Nov. 11, 2010

Related U.S. Application Data

(60) Provisional application No. 61/176,788, filed on May 8, 2009.

(51) Int. Cl.
*A61K 8/43* (2006.01)
*A61K 6/00* (2006.01)
*A61K 31/155* (2006.01)

(52) U.S. Cl.
USPC .......... 424/405; 424/616; 514/365; 514/642; 510/130

(58) Field of Classification Search
None
See application file for complete search history.

(56) References Cited

U.S. PATENT DOCUMENTS

| | | | |
|---|---|---|---|
| 4,592,488 A * | 6/1986 | Simon et al. | 222/94 |
| 4,879,281 A | 11/1989 | Shibasaki et al. | |
| 5,084,096 A | 1/1992 | Stovicek | |
| 5,378,226 A | 1/1995 | Hanifl et al. | |
| 5,408,022 A | 4/1995 | Imazato et al. | |
| 5,456,361 A | 10/1995 | Walsh et al. | |
| 5,541,165 A | 7/1996 | Turgeon | |
| 5,707,972 A | 1/1998 | Shimizu | |
| 5,709,866 A | 1/1998 | Booras et al. | |
| 5,958,381 A | 9/1999 | Curtis et al. | |
| 6,355,229 B1 | 3/2002 | Adamy | |
| 6,383,505 B1 | 5/2002 | Kaiser et al. | |
| 6,440,405 B1 | 8/2002 | Cooper et al. | |
| 6,562,360 B2 | 5/2003 | Scholz et al. | |
| 6,596,777 B1 | 7/2003 | Schiraldi et al. | |
| 6,949,958 B2 | 9/2005 | Zerbe et al. | |
| 2004/0247532 A1 | 12/2004 | Pinol et al. | |
| 2005/0058673 A1 | 3/2005 | Scholz et al. | |
| 2005/0169852 A1 | 8/2005 | Roberge et al. | |
| 2006/0051384 A1 | 3/2006 | Scholz et al. | |
| 2006/0051385 A1 * | 3/2006 | Scholz | 424/405 |
| 2006/0052452 A1 | 3/2006 | Scholz | |
| 2006/0057076 A1 | 3/2006 | Hino et al. | |
| 2006/0081486 A1 | 4/2006 | Klein et al. | |
| 2006/0088482 A1 | 4/2006 | Wulknitz et al. | |
| 2007/0014740 A1 | 1/2007 | Miller et al. | |
| 2007/0077211 A1 | 4/2007 | Sato et al. | |
| 2009/0032027 A1 | 2/2009 | McCachren et al. | |

FOREIGN PATENT DOCUMENTS

| | | |
|---|---|---|
| DE | 4113684 | 10/1992 |
| EP | 300961 | 6/1988 |
| EP | 372603 | 11/1989 |
| JP | 8119878 | 5/1996 |
| WO | 2004/080434 | 9/2004 |
| WO | 2005/000253 | 1/2005 |
| WO | 2005/022998 A2 | 3/2005 |
| WO | 2006/049620 | 5/2006 |
| WO | 2006/099359 | 9/2006 |

OTHER PUBLICATIONS

Franz et al., "Chlorhexidine gluconate (CHG) activity against clinical isolates of vancomycin-resistant *Enterococcus faecium* (VREF) and the effects of moisturizing agents on CHG residue assumulation on the skin", Journal of Hospital Infection, (1997) v. 37 pp. 157-164.

Greten, "inactivation of Residual CHG Activity by Thickened Alcohol Solution", Steris Corp, St Louis MO, Am J Infection Control, May 2004, p. E26.

Vorum, Henrik et. al., "Conventional Solubility Estimations" in Solubility of Long-Chain Fatty Acids in Phosphate Buffer at pH 7.4, *Biochimica et. Biophysica Acta.* 1126 (1992) 135-142.

Wlaschin, "Patents on Compatible Moisturizers for Oral Care, IPD-00002" Prepared on Feb. 10, 2009.

(Continued)

*Primary Examiner* — Frederick Krass
*Assistant Examiner* — Michael P Cohen

(57) ABSTRACT

A method of moisturizing while decolonizing mammalian tissue, the method comprising applying a multi-valent cationic antiseptic composition to the tissue, and applying a moisturizer composition to at least a portion of the same tissue; wherein the mammalian tissue is oral tissue of a subject; wherein the multi-valent cationic antiseptic is other than a metal ion; and wherein the applied compositions essentially exclude any component which causes a precipitate when combined with a multi-valent cationic antiseptic contained in the multi-valent cationic antiseptic composition when tested according to Test Method F, and/or wherein the moisturizer composition is such that a log reduction in the number of viable bacterial cells of at least 2 is provided when $10^6$ cfu of *Pseudomonas aeruginosa* are combined with a mixture 1.1 g of the moisturizer composition and 1.5 g of the multi-valent cationic antiseptic composition containing 0.12 weight percent of the multi-valent cationic antiseptic according to Test Method B; an oral care kit comprising a composition comprising the multi-valent cationic antiseptic and the moisturizer composition; and a method of moisturizing oral tissue of a patient requiring intubation using the moisturizer composition and an endotracheal tube coated or impregnated with a cationic antiseptic are provided.

18 Claims, 4 Drawing Sheets

OTHER PUBLICATIONS

Dufresne S, Hewitt, S. Robitaille *"Ozone sterilization: another option for healthcare in the 21st century"*. American Journal of Infection Control, vol. 32, Issue 3, May 2004, pp. E26-E27.

Sage Porducts Inc. website. Jun. 27, 2010 http://www.sageproducts.com/products/oral-hygiene/proven-to-address-vap.cfm#.

Sage Oral Hygiene Product Catalog. Sage Products Inc. 2010.

Medline "Oral Care Kit" Brochure. 2008 Medline Industries, Inc.

Kimberly Clark, "Kimvent Oral Care q4 Kit q2 Kit & Individual Components" Brochure 2008.

* cited by examiner

ORAL CARE METHOD AND KIT

This application claims the benefit of U.S. Provisional Application No. 61/176,788, filed May 8, 2009, which is incorporated herein by reference in its entirety.

BACKGROUND

Nosocomial pneumonias are a common hospital-acquired infection. The risk of such infections is believed to increase dramatically, for example, six to twenty fold, when mechanical ventilation is used on a patient. Ventilator associated pneumonia (VAP) is associated with high attributable mortality, which has been reported to be in the range of 33 to 50 percent. Published studies and Meta-Analysis have shown that oral care of mechanically ventilated patients with a chlorhexidine gluconate (CHG) containing mouth rinse significantly help reduce the incidence of VAP. Studies have also shown that dental plaque in ventilated patients becomes populated with pathogens which can then be aspirated, so removal and treatment of dental plaque is critical in the prevention of VAP. Ventilated patients as well as a significant segment of the population also suffer from xerostomia (dry mouth). Without the normal salivary flow, which not only mechanically washes off bacteria but also contains enzymes, antibodies, and other components important to the immune system, xerostomia favors bacterial proliferation. In the case of mechanically ventilated patients, the xerostomia has been treated by periodic application of a mouth moisturizer, while the CHG treatment mentioned above is intended to help reduce or prevent dental plaque, gingivitis, periodontal disease, as well as overgrowth of opportunistic microorganisms. In some instances, the mouth moisturizers dry out and become white or peelable upon drying. This is an undesirable characteristic, not only because health care workers have great concern about the general appearance of their patients, but it also decreases the efficacy of the moisturizer.

Certain oral hygiene products, for treating ventilated patients, are commercially available. Such products prepackage certain formulations and applicators, for example, mouth washes or rinses, oral debriding agents, mucosal moisturizers, swabs, and brushes.

However, there continues to be a need for improved methods and products which provide greater flexibility and efficacy in treating patients according to their individual indications.

SUMMARY OF THE INVENTION

The present invention provides a method of moisturizing while decolonizing mammalian oral tissue as well as an oral care kit and articles used therein for treating oral tissue. It has now been found, that oral tissue moisturizers presently used in commercial kits with a CHG oral rinse significantly reduce the antibacterial activity of the CHG oral rinse, and that components of these kits chemically inactivate the CHG. It is extremely important that any treatment regiment for mechanically ventilated patients address both the reduction of microorganisms (plaque removal and reduction of opportunistic organisms in the oral cavity) and xerostomia without having the products used for addressing these problems interact with each other to reduce the effectiveness of any one of the products when used in combination.

It has now also been found that certain oral tissue moisturizers can be selected, which when used with a CHG oral rinse do not reduce the antibacterial activity of the CHG rinse or reduce the antibacterial activity of the CHG rinse to a much lesser extent than oral tissue moisturizers presently used with a CHG oral rinse. We have further found that effective moisturizers can be formulated that can form soft flexible coatings that do not form self supporting films that may turn opaque and/or peel off. This applies as well to CHG oral gels and other CHG oral preparations.

Accordingly, in one embodiment, there is provided a method of moisturizing while decolonizing mammalian tissue, the method comprising:
  applying a multi-valent cationic antiseptic composition to oral tissue, and
  applying a moisturizer composition to at least a portion of the oral tissue;
  wherein the moisturizer composition essentially excludes any component which causes a precipitate when combined with a multi-valent cationic antiseptic used in the multi-valent cationic antiseptic composition when tested according to Test Method F;
  wherein the multi-valent cationic antiseptic is other than a metal ion.

In another embodiment, there is provided a method of moisturizing while decolonizing mammalian tissue, the method comprising:
  applying a multi-valent cationic antiseptic to the tissue, and
  applying a substantive moisturizer composition to at least a portion of the same tissue;
  wherein the mammalian tissue is oral tissue of a subject;
  wherein the multi-valent cationic antiseptic is other than a metal ion; and
  wherein the substantive moisturizer composition is such that a log reduction in the number of viable bacterial cells of at least 2 is provided when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent (0.00134 M) of the multi-valent cationic antiseptic according to Test Method B.

In another embodiment, there is provided an oral care kit comprising:
  a multi-valent cationic antiseptic composition comprising a multi-valent cationic antiseptic; and
  a moisturizer composition;
  wherein each composition is for application to oral tissue of a subject;
  wherein the moisturizer composition essentially excludes any component which causes a precipitate when combined with the multi-valent cationic antiseptic when tested according to Test Method F;
  wherein the multi-valent cationic antiseptic is other than a metal ion.

In another embodiment, there is provided an oral care kit comprising:
  a multi-valent cationic antiseptic composition comprising a multi-valent cationic antiseptic; and
  a substantive moisturizing composition;
  wherein each composition is for application to oral tissue of a subject;
  wherein the multi-valent cationic antiseptic is other than a metal ion; and
  wherein the substantive moisturizer composition is such that a log reduction in the number of viable bacterial cells of at least 2 is provided when $10^6$ cfu of *Pseudomonas aeruginosa* (ATCC 27853) are combined with a mixture of 1.1 g of the substantive moisturizer composition and 1.5 g of the multi-valent cationic antiseptic composition containing 0.12 weight percent of the multi-valent cationic antiseptic according to Test Method B.

For certain embodiments, including the above embodiments, the substantive moisturizer composition is such that a log reduction in the number of viable bacterial cells of at least 3 is provided. For certain of these embodiments, preferably the log reduction in the number of viable bacterial cells is at least 4, or even at least 5.

In another embodiment, there is provided a method of moisturizing while decolonizing mammalian tissue, the method comprising:

applying a multi-valent cationic antiseptic composition to the tissue, and applying a substantive moisturizer composition to at least a portion of the same tissue;

wherein the mammalian tissue is oral tissue of a subject;

wherein the multi-valent cationic antiseptic is other than a metal ion; and wherein when the substantive moisturizer composition includes an anionic compound, the anionic compound is such that the multi-valent cationic antiseptic composition combined with the substantive moisturizer composition achieves a log reduction in the number of viable bacterial cells of at least 2 when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent of the multi-valent cationic antiseptic according to Test Method B. For certain of these embodiments, the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

In another embodiment, there is provided a method of moisturizing while decolonizing mammalian tissue, the method comprising:

applying a multi-valent cationic antiseptic composition to the tissue, and applying a substantive moisturizer composition to at least a portion of the same tissue;

wherein the mammalian tissue is oral tissue of a subject;

wherein the multi-valent cationic antiseptic is other than a metal ion; and wherein when the substantive moisturizer composition includes an anionic compound, the anionic compound is such that greater than 40 percent of the multivalent cationic antiseptic, which was soluble in the multi-valent cationic antiseptic composition, remains soluble when the multi-valent cationic antiseptic composition and the substantive moisturizer composition are combined. For certain of these embodiments, the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

In another embodiment, there is provided an oral care kit comprising:

a multi-valent cationic antiseptic composition comprising a multi-valent cationic antiseptic; and a substantive moisturizing composition;

wherein each composition is for application to oral tissue of a subject;

wherein the multi-valent cationic antiseptic is other than a metal ion; and wherein when the substantive moisturizer composition includes an anionic compound, the anionic compound is such that the multi-valent cationic antiseptic composition combined with the substantive moisturizer composition achieves a log reduction in the number of viable bacterial cells of at least 2 when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent of the multi-valent cationic antiseptic according to Test Method B. For certain of these embodiments, the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

In another embodiment, there is provided an oral care kit comprising:

a multi-valent cationic antiseptic composition comprising a multi-valent cationic antiseptic; and a substantive moisturizing composition;

wherein each composition is for application to oral tissue of a subject;

wherein the multi-valent cationic antiseptic is other than a metal ion; and wherein when the substantive moisturizer composition includes an anionic compound, the anionic compound is such that greater than 40 percent of the multivalent cationic antiseptic which was soluble in the multi-valent cationic antiseptic composition remains soluble when the multi-valent cationic antiseptic composition and the substantive moisturizer composition are combined. For certain of these embodiments, the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

For certain embodiments, including any one of the above embodiments, the substantive moisturizer composition when dry does not form a self supporting film.

In another embodiment there is provided a method of moisturizing oral tissue of a patient requiring intubation, the method comprising:

applying a moisturizer composition to at least a portion of the oral tissue, an endotracheal tube, or both;

inserting an endotracheal tube through the patient's oral cavity and into the patient's trachea;

wherein the endotracheal tube is coated or impregnated with a cationic antiseptic;

wherein the moisturizer composition essentially excludes any component which causes a precipitate when combined with the cationic antiseptic when tested according to Test Method F; and wherein the cationic antiseptic is other than a metal ion.

DEFINITIONS

The following terms are used herein according to the following definitions.

"Oral tissue" refers to oral mucosal tissue, teeth, whether natural or prosthetic, within the oral cavity, tongue, and lips. For certain embodiments, preferably oral tissue is oral mucosal tissue.

"Mucosal tissue," "mucous membranes," and "mucosal membranes" and are used interchangeably and refer to the surfaces of the oral (e.g., mouth) cavity, and other similar tissues. Examples include mucosal membranes such as buccal and gingival mucosal membranes.

"Decolonizing" and "Decolonization" refer to a reduction in the number of microorganisms (e.g., bacteria) present in or on tissue that do not necessarily cause immediate clinical symptoms. Ordinarily fewer microorganisms are present in "colonized tissue" than in "infected tissue." When the tissue is completely decolonized the microorganisms have been "eradicated".

"Effective amount" means the amount of the one or more antiseptic components when in a composition, as a whole, provides antimicrobial (including, for example, antiviral, antibacterial, or antifungal) activity that when applied in an amount, at a frequency, and for a duration, reduces, prevents, or eliminates one or more species of microbes such that an acceptable level of the microbe results. Typically, this is a level low enough not to cause clinical symptoms, and is desirably a non-detectable level. It should be understood that in the compositions of the present invention, the concentrations or amounts of the components, when considered separately, may not kill to an acceptable level, or may not kill as broad a spectrum of undesired microorganisms, or may not kill as fast; however, when used together such components may provide an enhanced antimicrobial activity (as compared to the same components used alone under the same conditions). Also, it should be understood that (unless otherwise specified) the listed concentrations of the components are for "ready to use" or "as used" compositions. The compositions can be in a concentrated form. That is, certain embodiments of the compositions can be in the form of concentrates that would be diluted by the user with an appropriate vehicle.

"Hydrophilic" or "water-soluble" refers to a material that will dissolve in deionized water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60° C. for at least 4 hours and allowing this to cool to 23-25° C. for 24 hours, and mixing the composition thoroughly it appears uniform clear solution without visible cloudiness, phase separation, or precipitate in a jar having a path length of 4 cm. Typically when placed in 1×1 cm cell, the samples exhibit greater than 70% transmission measured in a suitable spectrophotometer at a wavelength of 655 nm.

"Hydrophobic" or "water-insoluble" refers to a material that will not significantly dissolve in deionized water at 23° C. "Not significantly" means that the solubility in water of the material is less than 5% by weight, preferably less than 1% by weight, more preferably less than 0.5% by weight, and even more preferably less than 0.1% by weight, based on the total weight of the hydrophobic material and the water. Solubility can be determined by thoroughly mixing the compound with water at the appropriate concentration at 23° C. for at least 24 hours (or at elevated temperature if that is necessary to dissolve the compound), allowing this to sit at 23-25° C. for 24 hours, and observing the sample. In a glass jar with a 4 cm path length the sample should have evidence of a second phase which can be liquid or solid and may be separated on the top, bottom, or distributed throughout the sample. For crystalline compounds care must be taken to avoid producing a supersaturated solution. The components should be mixed and observed. Cloudiness or presence of a visible precipitate or separate phase indicates that the solubility limit has been exceeded. Typically when placed in 1×1 cm cell the sample has less than 70% transmission measured in a suitable spectrophotometer at a wavelength of 655 nm. For solubility determinations less than that which can be observed with the naked eye, the solubility is determined using radiolabeled compounds as described under "Conventional Solubility Estimations" in *Solubility of Long-Chain Fatty Acids in Phosphate Buffer at pH* 7.4, Henrik Vorum, et. al., *Biochimica et. Biophysica Acta.* 1126 (1992) 135-142.

"Stable" means physically stable or chemically stable, which are both defined in greater detail below. Preferred compositions are both chemically and physically stable.

"Microorganism" or "microbe" or refers to bacteria, yeast, mold, fungi, protozoa, mycoplasma, as well as viruses (including lipid enveloped RNA and DNA viruses).

"Treat" or "treatment" means to improve the condition of a subject relative to the affliction, typically in terms of clinical symptoms of the condition.

"Subject" and "patient" includes humans, sheep, horses, cattle, pigs, dogs, cats, rats, mice, or other mammal.

"Enhancer" means a component that enhances the effectiveness of the antiseptic component such that when the composition less the antiseptic component and the composition less the enhancer component are used separately, they do not provide the same level of antimicrobial activity as the composition as a whole. For example, an enhancer component in the absence of the antiseptic component may not provide any appreciable antimicrobial activity. The enhancing effect can be with respect to the level of kill, the speed of kill, and/or the spectrum of microorganisms killed, and may not be seen for all microorganisms. In fact, an enhanced level of kill is most often seen in Gram negative bacteria such as *Escherichia coli*. An enhancer may be a synergist such that when combined with the remainder of the composition, the composition as a whole displays an activity that is greater than the sum of the activity of the composition less the enhancer component and the composition less the antiseptic component.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTIONS OF THE DRAWINGS

DETAILED DESCRIPTION OF ILLUSTRATIVE EMBODIMENTS

Figure 1:
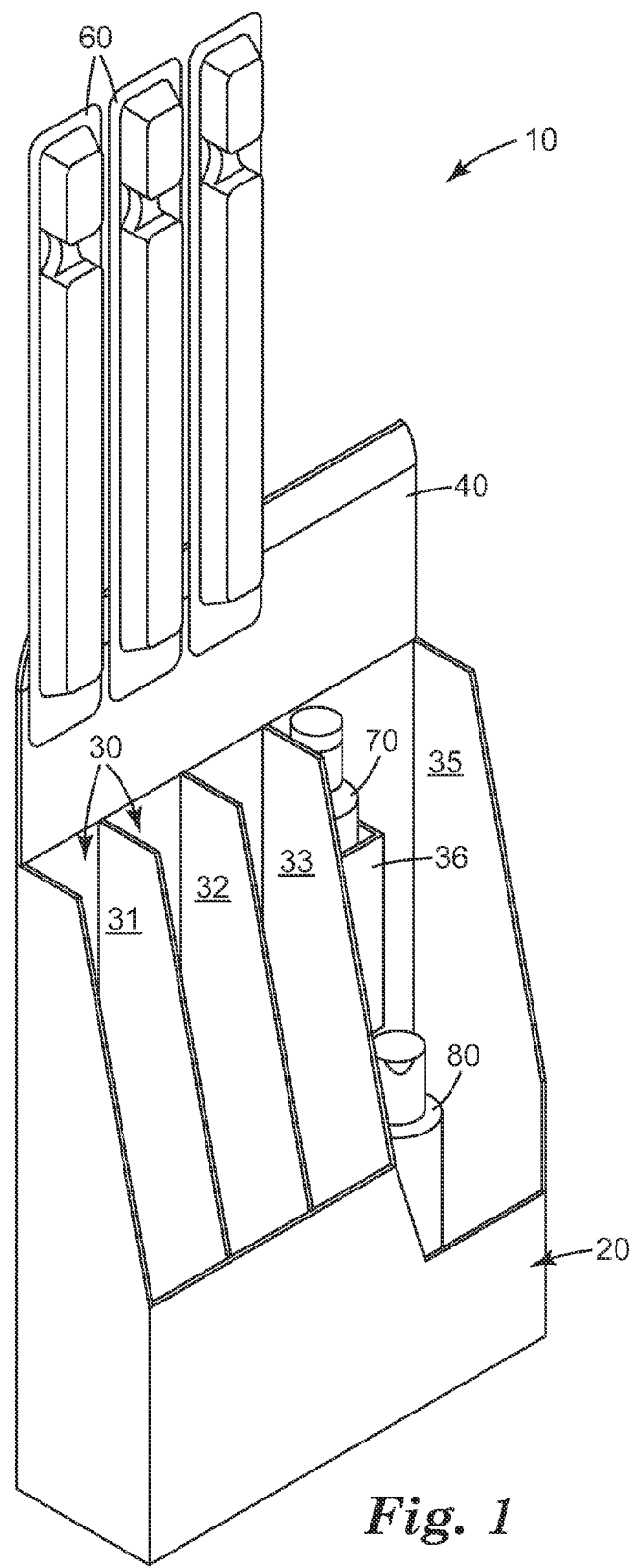
FIG. 1 is a perspective and partially exploded view of an oral care kit according to the present invention.

The present invention provides a method of moisturizing while decolonizing mammalian oral tissue. The present invention also provides an oral care kit and articles used therein for treating oral tissue, for example, using the present method of moisturizing while decolonizing oral tissue. The method and kit include a moisturizer or substantive moisturizer composition for moisturizing oral tissue. The moisturizer or substantive moisturizer composition can be used in combination with a multi-valent cationic antiseptic, for example, chlorhexidine salts such as CHG, without reducing the antibacterial activity of the multi-valent cationic antiseptic, or if reduced, the antibacterial activity of the multi-valent cationic antiseptic is reduced to a much lesser extent than oral tissue moisturizers presently used with a multi-valent cationic antiseptic oral rinse.

An oral tissue moisturizer that is compatible with CHG and in certain embodiments does not leave behind significant residue when repeatedly applied allows a user or practitioner a high degree of flexibility in meeting the individual oral care needs of the user or patient. Since xerostomia and patient oral health is influenced by factors such as hydration and medications, patients may have vastly different needs for oral moisturization. For example, the moisturizer or substantive moisturizer can be applied at the same time as the multi-valent cationic antiseptic, such as by including the multi-valent cationic antiseptic as part of the moisturizer formulation, thereby reducing the number of oral tissue applications. In another example, the moisturizer or substantive moisturizer can be applied at any time that there is an indication that the oral tissue is becoming too dry and could benefit from application of a moisturizer. Thus, the moisturizer or substantive moisturizer can be applied before, during, at the same time as, or after application of the multi-valent cationic antiseptic, while still providing or even maximizing the antibacterial benefits of the antiseptic, including the effect of the antiseptic to kill opportunistic microorganisms. In many instances, the multi-valent cationic antiseptic and moisturizer may be applied to the oral cavity 4 hours or less apart, for example, less than 120 minutes apart. In some instances they may be applied less than 60 minutes, 30 minutes, 15 minutes, or even 5 minutes apart. In some instances they may be applied simultaneously.

Multi-valent cationic antiseptics, such as CHG, can persist on oral tissue in the oral cavity for a number of hours, for example, for up to 5 hours. This persistence helps keep pathogenic bacterial counts low in the oral cavity and helps in the prevention of plaque and gingivitis, which is vital for the care of mechanically ventilated patients in hospitals. For certain embodiments, preferably this benefit can be sustained using the methods and kits described herein.

In the present methods, the multi-valent cationic antiseptic is applied as a composition comprising a solution of the multi-valent cationic antiseptic. For certain embodiments, the solution is an aqueous solution or a water/alcohol solution of the antiseptic. In other embodiments the multivalent cationic antiseptic is an emulsion such as a water in oil or oil in water emulsion.

Compositions used in conjunction with the multi-valent cationic antiseptic are prepared or selected to prevent or minimize interaction of the antiseptic with a material which precipitates the antiseptic and/or which can bind with or otherwise react with the antiseptic and neutralize its antibacterial activity. For certain embodiments, including any one of the above method or kit embodiments or any other embodiments thereof described herein, any composition applied to tissue or for application to tissue (e.g., moisturizer compositions, debriding compositions, multi-valent cationic antiseptic compositions, other oral care antiseptic compositions, or another oral care composition) essentially excludes any component which when combined with the multi-valent cationic antiseptic causes a precipitate to form which can be visibly observed.

In the embodiments described herein, whether or not a precipitate is formed can be determined using Test Method F as described below. An essentially excluded component is not present or is present in an amount such that when combined in that amount with the multi-valent cationic antiseptic no visually observable precipitate is formed. For certain of these embodiments, the essentially excluded component is not present.

As used herein, a precipitate is a separate phase, e.g., a solid, a gel, or a liquid that separates out from the antiseptic solution, wherein the precipitate includes multi-valent cationic antiseptic. When such a precipitate forms, the amount of multi-valent cationic antiseptic that remains soluble, and therefore active, may have been reduced. The degree to which the amount is reduced can be determined by assaying the amount of multi-valent cationic antiseptic in the solution in which it resides using standard analytical techniques, such a liquid chromatography, light absorbance, and/or other known methods. For example, Test Method C2 may be used as described below. For certain embodiments, preferably greater than 40 percent of the original amount of multi-valent cationic antiseptic remains in the solution. For certain of these embodiments, greater than 50, 60, or 70 percent, or even greater than 80, 90, or 95 percent of the original amount of multi-valent cationic antiseptic remains in the solution. For certain of these embodiments, the essentially excluded component is selected from the group consisting of polyanions of polycarboxylates, polysulfonates, polysulfates, and organic and inorganic polyphosphates; anions of alkylsulfates, arylsulfates, alkylsulfonates, arylsulfonates, alkylcarboxylates, arylcarboxylates, alkylphosphates, arylphosphates; halide salts; and combinations thereof, wherein the alkyl groups have a chain length of greater than 6 carbon atoms and the aryl groups have 6 or more carbon atoms. For certain of these embodiments, the essentially excluded component is not present or present at a concentration less than 0.1 percent by weight of the composition, except halide salts which are not present or present at a concentration not greater than 0.2 wt-% by weight of the composition. For certain of these embodiments, the essentially excluded component is selected from the group consisting of sodium saccharin, potassium sorbate, sodium benzoate, potassium chloride, sodium chloride, phosphoric acid, citric acid, sodium carboxymethylcellulose, carbomers, such as Carbomer 954, and glyceryl polymethacrylate. Alternatively or additionally, for certain of these embodiments, any composition applied to the oral tissue or for application to the oral tissue, for example, the moisturizer composition, is such that a log reduction in the number of viable bacterial cells of at least 2 is provided when $10^6$ cfu of *Pseudomonas aeruginosa* (ATCC 27853) are combined with a mixture of 1.1 g of the composition and 1.5 g of a multi-valent cationic antiseptic composition containing 0.12 weight percent of the multi-valent cationic antiseptic according to Test Method B. For certain embodiments, including the above embodiments, a log reduction in the number of viable bacterial cells of at least 3, preferably at least 4 or 5 is provided.

For certain embodiments, including any one of the above method or kit embodiments or any other embodiments thereof described herein, the moisturizer or substantive moisturizer composition is such that at least 35 percent, preferably at least 40 percent, more preferably greater than 40 percent, and for certain embodiments, preferably greater than 50 percent, more preferably greater than 60 percent, more preferably greater than 70 percent, and even more preferably greater than 80 percent of the multi-valent cationic antiseptic remains soluble when the multi-valent cationic antiseptic is combined with the moisturizer or substantive moisturizer composition in a weight ratio of 1 part moisturizer or substantive moisturizer composition to 1 part multi-valent cationic antiseptic composition containing the multi-valent cationic antiseptic. The amount of the multi-valent cationic antiseptic that remains soluble can be determined, for example, by measuring the amount that can be recovered from a mixture of the moisturizer or substantive moisturizer composition and the multi-valent cationic antiseptic within 4 hours with a mixture of water and methanol according to Test Method C. For certain embodiments, including any one of the above method or kit embodiments or any other embodiments thereof described herein, the moisturizer or substantive moisturizer composition is such that at least 35 percent, preferably at least 40 percent, more preferably greater than 40 percent of the multi-valent cationic antiseptic remains soluble and can be recovered from a mixture of the moisturizer or substantive moisturizer composition and the multi-valent cationic antiseptic within 4 hours with a mixture of water and methanol according to Test Method C. For certain of these embodiments, greater than 50 percent, greater than 60 percent, greater than 70 percent, or greater than 80 percent of the multi-valent cationic antiseptic remains soluble and can be recovered. It is understood, however, that the solvent system should be considered and optimized for each composition to ensure that control samples of known cationic antiseptic concentration in the same range as the test sample achieve complete recovery of the cationic antiseptic. For example, water and acetonitrile may also be used instead of water and methanol, and trifluoroacetic acid (TFA), formic acid, ammonium acetate, or ammonium formate may be used with these solvent mixtures. One skilled in the art will know how to modify the solvent system.

For certain embodiments, including any one of the above method or kit embodiments or any other embodiments thereof described herein, the moisturizer or substantive moisturizer composition essentially excludes a component selected from the group consisting of polyanions such as polycarboxylates, polysulfonates, polysulfates, and polyphosphates; chelators; inorganic buffers; anions such as alkylsulfates, arylsulfates, alkylsulfonates, arylsulfonates, alkylcarboxylates, arylcarboxylates, alkylphosphates, arylphosphates; and combinations thereof. Alkyl groups referred to here include those having a chain length of greater than four carbon atoms, preferably alkyl groups of 6 or more carbon atoms, preferably greater than 6 carbon atoms. Aryl groups referred to here include those having 6 or more carbon atoms. Anions including such alkyl and aryl groups, which do not include hydroxyl groups or other polar solubilizing groups, may precipitate the multi-valent cationic antiseptic from solution. "Polyanion" as used herein is a small molecule oligomer, or polymer having, on average, at least two ionic groups (e.g., carboxylate, sulfate, sulfonate, or phosphate group) per molecule. For certain embodiments, halide salts at a concentration greater than 1 wt-%, 0.5 wt-%, or 0.2 wt-% by weight of the composition in a combination of the multi-valent cationic antiseptic and the moisturizer or substantive moisturizer composition are further essentially excluded. For certain of these embodiments, the essentially excluded component is selected from the group consisting of sodium saccharin, potassium sorbate, sodium benzoate, potassium chloride, sodium chloride, phosphoric acid, citric acid, sodium carboxymethylcellulose, carbomers, such as Carbomer 954, and glyceryl polymethacrylate. Essentially excluded components are not present or are present in amounts which allow for at least a 2 log reduction determined according to Test Method B. Alternatively, or in addition, essentially excluded components are not present or are present in amounts such that at least 35 percent, preferably at least 40 percent, more preferably greater than 40 percent, of the multi-valent cationic antiseptic remains soluble and can be recovered from a mixture of the moisturizer or substantive moisturizer composition and the multi-valent cationic antiseptic within 4 hours with a mixture of water and methanol according to Test Method C. For certain of these embodiments, greater than 50 percent, greater than 60 percent, greater than 70 percent, or greater than 80 percent of the multi-valent cationic antiseptic remains soluble and can be recovered. For certain of these embodiments, the essentially excluded components are not present.

For certain embodiments, including any one of the above method or kit embodiments or any other embodiments thereof described herein, preferably when the moisturizer or substantive moisturizer composition includes an anionic compound, the anionic compound is such that a log reduction in the number of viable bacterial cells of at least 2 is provided when $10^6$ cfu of *Pseudomonas auerginosa* are combined with a mixture of 1.1 g of the moisturizer or substantive moisturizer composition and 1.5 g of a multi-valent cationic antiseptic composition containing 0.12 weight percent of the multi-valent cationic antiseptic according to Test Method B. Alternatively, or in addition, preferably when the moisturizer or substantive moisturizer composition includes an anionic compound, the anionic compound is such that greater than 40 percent of the multivalent cationic antiseptic is soluble when the multi-valent cationic antiseptic and the moisturizer or substantive moisturizer composition are combined. Preferably greater than 50 percent, greater than 60 percent, greater than 70 percent, or greater than 80 percent of the multi-valent cationic antiseptic remains soluble. Here, if possible, the anionic compound is selected and used in an amount such that these conditions are met. For certain of these embodiments, the anionic compound is selected from the group consisting of polyanions such as polycarboxylates, polysulfonates, polysulfates, and polyphosphates; chelators; inorganic buffers; anions such as alkylsulfates, arylsulfates, alkylsulfonates, arylsulfonates, alkylcarboxylates, arylcarboxylates, alkylphosphates, arylphosphates; and combinations thereof. Alkyl groups referred to here include those having a chain length of greater than six carbon atoms. However, alkyl groups of four or less carbon atoms may increase the likelihood that the above amounts of multi-valent cationic antiseptic remains soluble in the presence of such anions. Aryl groups referred to here include those having 6 or more carbon atoms. Anions including such alkyl and aryl groups, which do not include hydroxyl groups or other polar solubilizing groups, may precipitate the multi-valent cationic antiseptic from solution. "Polyanion" as used herein is a small molecule oligomer, or polymer having, on average, at least two ionic groups (e.g., carboxylate, sulfate, sulfonate, or phosphate group) per molecule. For certain embodiments, the group from which the anionic compound is selected further includes halide salts at a concentration greater than 0.2 wt-% by weight of the composition.

For certain embodiments, any other composition described herein and used in combination with the multi-valent cationic antiseptic, for example, a de-briding composition, also essentially excludes these materials and components.

For optimal multi-valent cationic antiseptic activity, for example, maximizing antimicrobial effectiveness, the pH of the moisturizer or substantive moisturize is preferably in the mildly acidic to approximately neutral range. For certain embodiments, including any one of the above embodiments, the moisturizer or substantive moisturizer composition has a pH of 3 to 8 or 4 to 8. For certain of these embodiments, the pH is at least 4.5, at least 5, or at least 6. For certain of these embodiments, the pH is not greater than 7.5, preferably not greater than 7. For certain of these embodiments, the pH is 4.5 to 7, preferably 6 to 7.

Because of the presence of saliva and/or mucus secretions as well as other medicaments or compositions that may be administered in the oral environment, the moisturizer is preferably substantive to resist being washed or dislodged from the oral tissue for a period of time. For certain embodiments, preferably at least a portion of the applied substantive moisturizer remains at the site of application for at least 1 hour, at least 2 hours, or more preferably at least 4 hours. Substantivity may by evaluated using Test Method E described below. Relatively high viscosities are preferred to reduce migration as well as to provide substantivity (resistance to removal by fluids) to ensure moisturization for long periods of time. In certain embodiments, including any one of the above embodiments, the substantive moisturizer composition has a viscosity of at least 20 centipoise (cps), preferably at least 50 cps, preferably at least 100 cps, more preferably at least 500 cps. For certain of these embodiments, the substantive moisturizer composition has a viscosity of at least 1,000 cps, more preferably at least 10,000 cps. Most preferred compositions have viscosities of at least 20,000 cps, more preferably in excess of 50,000 cps. For certain embodiments, the viscosity can be at least 100,000 cps or even at least 1,000,000. These viscosities can be conveniently measured by the Viscosity Test (Test Method A) described herein. Compositions meet these viscosity values at 22-25° C., and in certain embodiments even after heating to 32° C., 35° C. or as high as 37° C., so that when in contact with mammalian tissue the compositions remain substantive. For certain of these embodiments, preferably the substantive moisturizer composition includes a hydrophobic component (e.g., as described below) and/or a polyhydroxy compound and can be spread evenly across the tissue. Clearly, it is also important that the composition wet the tissue in order to easily coat the tissue without dewetting. This can be critical to achieving substantivity. Wetting can be achieved by adjusting the vehicle components and/or addition of surfactant(s).

In order to further enhance substantivity of the compositions, for certain embodiments, polycationic polymers are included in the moisturizer composition. These are not only compatible with the multivalent cationic antiseptic and improve retention by increasing viscosity, but they also increase retention or substantivity by ionically binding with the oral tissue.

Moreover, for certain embodiments, hydrophobic water insoluble components are included to increase retention. For example, high oil in water emulsions or water in oil emulsions can resist removal from mucosal tissue due to the water insoluble nature of the oil. Suitable oils include any of the hydrophobic emollients and emulsifiers disclosed in U.S. Pat. No. 6,562,360. In particular, use in the oral cavity of those emollients and emulsifiers that are approved for use as food additives are particularly preferred. For example, C8 to C18 mono-, di- and tri-esters of glycerin and propylene glycol may be used as well as a variety of edible oils such as vegetable oils.

Compositions comprising the multi-valent cationic antiseptic, alone or in combination with the moisturizer or substantive moisturizer composition, can provide at least a 2 log reduction in the number of viable bacterial cells of at least one type of bacteria. Bacterial reduction is generally reported as $\log_{10}$ reduction determined by the difference between the $\log_{10}$ of the initial inoculum count and the $\log_{10}$ of the inoculum count after exposure to the multi-valent cationic antiseptic. For certain embodiments, compositions comprising the multi-valent cationic antiseptic included in the methods and kits of the present invention provide an average of at least a 2 log reduction in a test bacteria 30 minutes, preferably in 10 minutes, more preferably in 2.5 minutes. For certain of these embodiments, compositions comprising the multi-valent cationic antiseptic, alone or in combination with the moisturizer or substantive moisturizer composition, provide an average of at least a 3 log reduction, preferably at least a 4 log reduction in the test bacteria.

A bacterial assay can be used to determine when a composition comprising a multi-valent cationic antiseptic alone or in combination with a moisturizer or substantive moisturizer composition provides sufficient antimicrobial activity. One readily performed assay involves exposing a selected known or readily available viable microorganism strain, such as *Enterococcus* spp., *Aspergillus* spp., *Escherichia* spp. (e.g., *E. coli*), *Staphylococcus* spp. (e.g., *Staphylococcus aureus*), *Streptococcus* spp. (e.g., *Streptococcus pneumonia*), *Pseudomonas* spp. (e.g., *Pseudomonas aeruginosa*), *Enterobacter* spp., or *Salmonella* spp., or other microorganism such as *Haemophilus influenza* or *Acinetobacter baumannii*, to a test composition at a predetermined bacterial burden level in a culture media at an appropriate temperature. This may be conveniently carried out using the Test Method B described in the Examples Section. Briefly, in Test Method B, approximately $10^6$ cfu's are inoculated into a multi-valent cationic antiseptic composition, or a moisturizer composition mixed with a multi-valent cationic antiseptic composition, or a moisturizer composition which includes a multi-valent cationic antiseptic. After incubation for a specific time period, the mixture is neutralized and enumerated by dilution plating.

Compositions comprising the multi-valent cationic antiseptic alone or in combination with the moisturizer or substantive moisturizer composition may provide residual antimicrobial efficacy by maintaining an average log reduction of at least 1 log, more preferably at least 1.5 log, and even more preferably at least 2 log, for at least 1 hour, more preferably at least 2 hours, and even more preferably at least 4 hours after application to oral tissue.

Multi-valent cationic antiseptics, such as chlorhexidine, kill both gram-positive and gram-negative microbes. In addition, they are active against lipid enveloped viruses and fungi. At least one mechanism of action is believed to be membrane disruption. Examples of relevant microorganisms against which the antiseptics are active, although not necessarily those normally encountered in the oral cavity, include *Staphylococcus* spp., *Streptococcus* spp., *Pseudomonas* spp., *Enterococcus* spp., and *Esherichia* spp., *Aspergillus* spp., *Fusarium* spp., *Acinetobacter* spp., and *Candida* spp. Particularly virulent organisms include *Staphylococcus aureus* (including resistant strains such as Methicillin Resistant *Staphylococcus Aureus* (MRSA), *Staphylococcus epidermidis, Streptococcus mutans, Streptococcus pneumoniae, Enterococcus faecalis*, Vancomycin Resistant *Enterococcus* (VRE), *Pseudomonas aeruginosa, Escherichia coli, Aspergillus niger, Aspergillus fumigatus, Aspergillus clavatus, Fusarium solani, Fusarium oxysporum, Fusarium chlamydosporum, Candida albicans, Candida glabrata*, and *Candida krusei*. For certain embodiments, those microorganisms relevant to the oral cavity and oral tissue, for example, of a mechanically ventilated subject, include *Staphylococcus aureus, Streptococcus pneumonia, Pseudomonas aeruginosa, Haemophilus influenza* and *Acinetobacter baumannii*, and *Enterobacter* spp.

For certain embodiments, including any one of the above embodiments, the multi-valent cationic antiseptic is selected from the group consisting of biguanides, bisbiguanides, polybiguanides, polymeric quaternary ammonium compounds, and combinations thereof. Biguanides include the following 2-carbamimidoylguanidine structure of formula (I):

wherein at least one of $R^1$, $R^2$, $R^3$, and $R^4$ is an alkyl, aryl, or arylalkyl group, and any remaining $R^1$, $R^2$, $R^3$, or $R^4$ groups are hydrogen.

Bisbiguanides include the following bis(2-carbamimidoylguanidine) structure of formula (II):

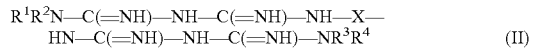

wherein at least one of $R^1$, $R^2$, $R^3$, and $R^4$ is an alkyl, aryl, or arylalkyl group, and any remaining $R^1$, $R^2$, $R^3$, or $R^4$ groups are hydrogen, and X is a divalent connecting group, for example a straight-chain or branched $C_{3-10}$ alkylene group, optionally interrupted with —O—, —S—, or arylene (e.g., phenlyene, naphthylene), preferably straight-chain $C_{4-8}$ alkylene preferably straight-chain hexylene.

At least one of $R^1$ and $R^2$ and at least one of $R^3$ and $R^4$ is preferably hydrogen. Alkyl groups include, for example, $C_{1-18}$ alkyl groups, preferably $C_{1-8}$ alkyl groups. Aryl groups include $C_{6-10}$ aryl groups, preferably phenyl groups. Arylalkyl groups include any combination of these alkyl and aryl groups, for example, benzyl and 2-phenylethyl. Any of these groups may be substituted with one or more halo, nitro, $C_{1-4}$ alkyl, $C_{1-4}$ alkoxy, $C_{4-9}$ cycloalkyl, or a combination thereof.

Polybiguanides include the following polymeric structure of formula (III) wherein X is as described above; Z is a terminal group such as an amino group or salt thereof, a dicyandiamido group or a cyanoguanidino group; and n is at least 3 and not more than about 50, preferably at least 4 and not more than about 40, more preferably at least 5 and not more than 20:

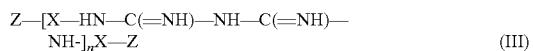

Examples of biguanides of formula (I) include but are not limited to Metformin ($R^1$ and $R^2$=methyl), Buformin ($R^1$=n-butyl, Phenformin ($R_1$=2-phenylethyl), and the like. Examples of bisbiguanides of formula (II) include but are not limited to chlorhexidine (X is —$(CH_2)_6$—, and $R^1$ and $R^3$ are 4-chlorophenyl) and alexidine (1,1'-hexamethylene-bis[5-(2-ethylhexyl)biguanide]) and their various salts such as the digluconate, diacetate, dimethosulfate, and dilactate salts as well as combinations thereof. Examples of polybiguanides include but are not limited to PHMB (poly(hexamethylenebiguanide)) and salts thereof. In one preferred form, PHMB is commercially available as Cosmocil CQ from Arch Chemicals Inc., Smyrna Ga.

Polymeric quaternary ammonium compounds include polymers having quaternary amine groups with at least one alkyl or aralkyl chain of at least 6 carbon atoms and preferably as least 8 carbon atoms. The polymers may be linear, branched, hyperbranched or dendrimers. Examples of antimicrobial polymeric quaternary amine polymers include but are not limited to quaternary ammonium functionalized dendrimers such as those described in U.S. Pat. No. 6,440,405; polymers which are the polymerization product of quaternary ammonium functional (meth)acrylate monomers such as those described in U.S. Pat. No. 5,408,022; polyethers, polycarbonates, and polyurethanes prepared from quaternary ammonium functional diols such as those described in U.S. Pat. No. 5,084,096; and the like Any soluble salt of the multi-valent cationic antiseptic, including the above described salts, may be used. For example, where hydrochloride salts are soluble, such salts are suitable.

"Soluble" as used herein with respect to the multi-valent cationic antiseptic and/or salts thereof refers to solubility in a composition, for example, an aqueous fluid, above the minimum inhibitory concentration (MIC) of the treatment microorganism. If the solubility limit is less than the MIC, treatment may be ineffective. Preferably the solubility exceeds the minimum bacteriacidal concentration (MBC).

For certain embodiments, including any one of the above embodiments, preferably the multi-valent cationic antiseptic is a bisbiguanide or a polybiquanide. For certain of these embodiments, the multi-valent cationic antiseptic is chlorhexidine or PHMB. For certain of these embodiments, the multi-valent cationic antiseptic is PHMB. Alternatively, for certain of these embodiments, the multi-valent cationic antiseptic is chlorhexidine. The multi-valent cationic antiseptic may be present as the free base, but is preferably present as a soluble salt. For example, chlorhexidine may be present as the free base but is preferably present as a disalt of acetate, gluconate, lactate, methosulfate ($CH_3OSO_3^-$), or combinations thereof. These salts all have solubility limits in water in excess of 1 g/100 ml. For example, the solubility limit of the digluconate salt is 20 g/100 ml and that of the diacetate is 1.9 g/100 ml. For certain of these embodiments, preferably the multi-valent cationic antiseptic is chlorhexidine digluconate (CHG). In one alternative, preferably the multi-valent cationic antiseptic is the hydrochloride of PHMB.

The multi-valent cationic antiseptics are dissolved in an aqueous carrier, for example water or water and an alcohol, a non-aqueous carrier, or a combination thereof and protected from light. Protection from light and use of a non-aqueous carrier may help reduce the degradation of susceptible antiseptic compounds over time. When used in compositions comprising less than about 20% by weight water, these antiseptics are preferably formulated with a hydrophilic carrier that solubilizes the antiseptic. Examples of suitable solvents for many multivalent cationic antiseptics, including chlorhexidine gluconate, include glycols (compounds having at least two hydroxyl groups per molecule) such as PEGs having a molecular weight below 2000 and preferably less than 1000 and most preferably less than about 800 daltons; glycerin and polyglycerols, propylene glycol, dipropylene glycol, tripropylene glycol, polypropylene glycol, ethylene oxide/propylene oxide random or block copolymers, trimethylolpropane, pentraerythritol, sorbitol, panetothenol, glucuronolactone, gluconic acid, and the like as well as other polar solvents such as N-methyl pyrrolidone, propylene carbonate, butyrolactone and the like.

Care may be taken when formulating chlorhexidine as well as other multi-valent cationic antiseptic compounds to avoid inactivation by sequestering it in micelles which may be formed by incorporation of surfactants and/or emulsifiers (for example, certain nonionic surfactants). Some examples of formulations that may be used include hydrophilic ointments; aqueous solutions thickened with polymeric thickeners that are either surfactant free or contain surfactants that do not reduce the activity of the CHG, such as certain poloxamers; and ointments comprising a major amount of a hydrophobic component and preferably further comprising a hydrophilic component.

The multi-valent cationic antiseptics, such as chlorhexidine, are very basic and capable of forming multiple ionic bonds with anionic materials. For this reason, the multi-valent cationic antiseptic compositions, as well as the moisturizer or substantive moisturizer compositions and other compositions used in combination with the antiseptic compositions are preferably free of anionic compounds that can result in precipitation of the antiseptic. Also, thickener systems, if present, are preferably based on non-ionic and/or cationic polymers or emulsifiers. Anionic surfactants useful, for example, as wetting agents, may also need to be avoided. Certain zwitterionic, very water soluble, or non-precipitating anionic emulsifiers and surfactants may be useful. Although halide salts were previously believed to cause CHG to precipitate, it has now been found that salts, such as sodium chloride may be used at levels up to 0.2 percent by weight of the composition. Therefore, if a system includes CHG or other multi-valent cationic antiseptic, and needs to comprise salts for stability or other purposes, the salt should be evaluated for compatibility with the multi-valent cationic antiseptic. For example, the inhibitory levels of certain reagents like salt or anionics can be different from CHG for a polymeric guanide such as PHMB and would require testing. However, gluconate salts such as triethanolamine gluconate or sodium gluconate, can be used with CHG. Furthermore, if an additional antiseptic is incorporated into the composition it is preferably non-ionic or cationic. If it is cationic the counter ion should be compatible with both antiseptics ensuring solubility of both. Attention may be paid to the pKa, pH, acid equivalents, and solubility of polymer in question when potentially inhibitory compounds are used in the formulation. However, these criteria may be insufficient to determine if sufficient kill can be obtained when a cationic antiseptic is used with a moisturizer or substantive moisturizer.

For certain embodiments, including any one of the above embodiments, the multi-valent cationic antiseptic is included in a composition at a sufficient concentration such that when applied to mammalian tissue for an adequate time, for an adequate frequency, and in an adequate dose the antiseptic can provide at least a 2 log reduction, decolonize, or eradicate at least one microorganism from the oral tissue. For certain of these embodiments, the concentration is at least 0.05 weight percent (wt-%). For example, for certain embodiments, the moisturizer or substantive moisturizer composition contains 0.05 wt-% of a multi-valent cationic antiseptic as a preservative. For certain of these embodiments, the concentration is at least 0.1 wt-%. For certain of these embodiments, the multi-valent cationic antiseptic is included in a composition at a concentration of no greater than 2 wt-%, no greater than 1 wt-%, no greater than 0.5 wt-%, no greater than 0.4 wt-%, or no greater than 0.20 wt-%. For certain of these embodiments, the multi-valent cationic antiseptic is included in a composition comprising a solution of the multi-valent cationic antiseptic at 0.05 to 0.4 weight percent. For certain of these embodiments, the multi-valent cationic antiseptic is included in a composition comprising a solution of the multi-valent cationic antiseptic at 0.1 to 0.2 weight percent. For certain of these embodiments, the multi-valent cationic antiseptic is included in a composition comprising a solution of the multi-valent cationic antiseptic at 0.12 weight percent in water and alcohol. In one example, the composition is commercially available as PERIDEX (0.12 wt-% chlorhexidine gluconate, 3M Health Care, St. Paul, Minn.).

The multi-valent cationic antiseptics may be used alone, in combination, or with other antiseptics in order to effectively kill microorganisms on oral tissue. Additional antiseptics for use with the multi-valent cationic antiseptic include peroxides, antimicrobial natural oils, and compatible combinations thereof as provided in U.S. Patent Application Publication No. 2006/0051384 A1; diphenyl ethers, phenols, halogenated phenols, bisphenols, resorcinols and its derivatives, anilides, and combinations thereof, provided in U.S. Patent Application Publication No. 2006/0052452 A1. Also, antimicrobial lipid antiseptics may additionally be used. Such antimicrobial lipids include (C7-C14)saturated fatty acid esters of a polyhydric alcohol, (C8-C22)unsaturated fatty acid esters of a polyhydric alcohol, (C7-C14)saturated fatty ethers of a polyhydric alcohol, (C8-C22)unsaturated fatty ethers of a polyhydric alcohol, and alkoxylated derivatives thereof, or combinations thereof, wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or combinations thereof. Useful antiseptics of this class are further described in U.S. Patent Application Publication No. 2005/0058673. As used herein the term "fatty" refers to alkyl and alkylene hydrocarbon chains of odd or even number of carbon atoms from C6-C18.

Alternatively, the antimicrobial lipid can be a (C8-C12) fatty alcohol ester of a (C2-C8)hydroxycarboxylic acid (also often referred to as a (C2-C8)hydroxycarboxylic acid ester of a (C8-C12)fatty alcohol), a (C8-C22)mono- or poly-unsaturated fatty alcohol ester of a (C2-C8)hydroxycarboxylic acid (also often referred to as a (C2-C8)hydroxycarboxylic acid ester of a (C8-C22)mono- or poly-unsaturated fatty alcohol), or alkoxylated derivatives thereof. The alkoxylated derivatives have less than 5 moles of alkoxide per mole of polyhydric alcohol or hydroxy acid. The hydroxycarboxylic acid moiety can include aliphatic and/or aromatic groups. For example, fatty alcohol esters of salicylic acid are possible.

As used herein, a "fatty alcohol" is an alkyl or alkylene monofunctional alcohol having an even or odd number of carbon atoms and a "fatty acid" is an alkyl or alkylene monofunctional carboxylic acid having an even or odd number of carbon atoms.

Cationic antiseptic compositions may have a persistently bitter taste. It has now been found that certain non-ionic sweetening compounds can be used together with the multi-valent cationic antiseptic to significantly reduce this bitter taste without significantly diminishing antiseptic activity. We have found that anionic sweeteners employed in these compositions previously, such as sodium saccharin, can precipitate cationic actives such as chlorhexidine gluconate. We believe this would be true for many cationic antiseptics. For certain embodiments, including any one of the method or oral care kit embodiment described herein, the composition including the multi-valent cationic antiseptic further comprises a sweetener selected from the group consisting of sucralose, aspartame, sugars and sugar alcohols including but not limited to xylose, sucrose, maltose, mannose, glucose, xylitol, sorbitol, mannitol, erythritol, maltitol, lactitol, and a combination thereof.

For certain embodiments, compositions comprising the multi-valent cationic antiseptic also include at least one additional component selected from the group consisting of enhancers, surfactants, hydrophilic compounds, hydrophobic compounds, and combinations thereof.

Compositions used in the present method and kit can be applied with swabs, cloth, sponges, foams and non-woven and paper products (e.g., paper towels and wipes), for example where they are used to deliver a significant portion of the antiseptic composition to the oral tissue. By "significant portion" it is meant that enough composition is applied and allowed to remain on the tissue when applied in a dose, at a frequency, and in an amount sufficient to reduce or eliminate the microorganisms on or in the tissue.

Compositions used in the present method and kit are physically stable. As defined herein "physically stable" compositions are those that do not significantly change due to substantial precipitation, crystallization, phase separation, and the like, from their original condition during storage at 25° C. for at least 3 months, and preferably for at least 6 months. Particularly preferred compositions are completely physically stable if a 10-milliliter (10-ml) sample of the composition when placed in a 15-ml conical-shaped graduated plastic centrifuge tube (Corning) and centrifuged at about 2275×g (e.g. 3,000 revolutions per minute (rpm) for 10 minutes using a Labofuge B, model 2650 manufactured by Heraeus Sepatech GmbH, Osterode, West Germany) or similar centrifuge at a centrifugal force of 2275×g has no visible phase separation in the bottom or top of the tube. Phase separation of less than 0.5 ml is also considered stable as long as there is no other sign of physical separation in the sample.

Compositions used in the present method and kit exhibit good chemical stability. This can be a concern with compounds that may hydrolyze or undergo heat and/or light degradation such as chlorhexidine. The most preferred compositions retain an average of at least 97% of the antiseptic component after aging for 4 weeks at 40° C. in a sealed container beyond the initial 5-day equilibration period at 25° C. The percent retention is understood to mean the weight percent of antiseptic component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 25° C. for five days. The level of antiseptic component is preferably determined using gas chromatography or high performance liquid chromatography using appropriate standards and controls.

In the present methods, the multi-valent cationic antiseptic is applied as a composition comprising a solution of the multi-valent cationic antiseptic. For certain embodiments, the solution is an aqueous solution or a water/alcohol solution of the antiseptic.

As indicted above, the multi-valent cationic antiseptic is included in a composition comprising a solution of the multi-valent cationic antiseptic, and for certain embodiments, the solution is an aqueous solution or a water/alcohol solution of the antiseptic. The composition may additionally include various other materials as described herein. Alternative compositions where the multi-valent cationic antiseptic is dissolved in or mixed with a non-aqueous hydrophilic material are also contemplated.

The moisturizer or substantive moisturizer composition may be used or provided in various forms including, for example, hydrophobic ointments, oil in water emulsions, water in oil emulsions, thickened aqueous gels, and hydrophilic gels.

Hydrophobic compositions include a hydrophobic base or vehicle (e.g., petrolatum, insoluble oils, thickened or gelled water insoluble oils and the like) and may include a minor amount of a water-soluble phase, which would include the multi-valent cationic antiseptic if present. Acceptable salts, surfactants, emulsifiers, humectants and/or other components may also be included. Care must be taken to ensure that the composition does not degrade or negatively effect the endotracheal tube used for ventilation or other medical devices that may be in contact or in proximity to the mucosal tissue. Certain hydrophobic components can degrade plasticized PVC which is commonly used as endotracheal tube material. Preferably the compositions do not negatively effect natural rubber latex or nitrile gloves.

Oil in water emulsion compositions include a discrete phase of a hydrophobic component and a continuous aqueous phase comprising water and optionally one or more polar hydrophilic carriers, where either or both phases include the multi-valent cationic antiseptic if present. Acceptable salts, surfactants, emulsifiers, humectants, and/or other components may also be included. These emulsions may comprise acceptable water-soluble or water swellable polymers as well as one or more emulsifiers that help to stabilize the emulsion.

Water in oil emulsion compositions include a continuous phase of a hydrophobic component and an aqueous phase comprising water and optionally one or more polar hydrophilic carriers as well as acceptable salts or other components, where the multi-valent cationic antiseptic if present is in either or both phases. Acceptable salts, surfactants, emulsifiers, humectants and/or other components may also be included. These emulsions may comprise oil soluble or oil swellable polymers and one or more emulsifiers, as well as inorganic salts such as magnesium sulfate, that help to stabilize the emulsion.

Thickened aqueous gel compositions include an aqueous phase, which would include the multi-valent cationic antiseptic if present, that has been thickened to achieve a sufficiently high viscosity as described above, for example, a viscosity of at least 10 cps and preferably at least 20 cps. Viscosities of at least 50 cps, at least 100 cps, at least 250 cps, or at least 500 cps may also be preferred. The viscosity is determined using the Viscosity Test described herein. These compositions are thickened by suitable natural, modified natural, or synthetic polymers as described below. The thickened aqueous gels can also be thickened using suitable emulsifiers such as alkyl alcohols and polyethoxylated alkyl chain surfactants that effectively thicken the composition. Examples include the Polawax, Behenyl TMS, Crodaphos CES, Cosmowax, and Crothix systems from Croda Inc.

Hydrophilic gel compositions include a continuous phase comprised of at least one water soluble hydrophilic component other than water. The formulations may contain water up to 90% by weight. The higher concentrations may be suitable in some compositions. Suitable hydrophilic components are described below under the heading "Hydrophilic Component." For certain embodiments, suitable hydrophilic components include one or more glycols (such as glycerin, propylene glycol, butylenes glycol, etc.), polyethylene glycols (PEG), random or block copolymers of ethylene oxide, propylene oxide, and/or butylenes oxide, polyalkoxylated surfactants having one or more hydrophobic moieties per molecule, silicone copolyols, as well as combinations thereof. One skilled in the art will recognize that the level of ethoxylation must be sufficient to render the hydrophilic component water-soluble or water dispersible at 23° C.

As indicated above, the present methods and kits can provide a significant advancement in antimicrobial effectiveness as well as flexibility in applying the moisturizer composition as needed by a patient. Because the moisturizer or substantive moisturizer composition maintains the antimicrobial effectiveness of the multi-valent cationic antiseptic, the moisturizer can be applied at any time in the presence of the antiseptic. For certain embodiments, including any one of the above method embodiments, the moisturizer or substantive moisturizer composition is applied after applying the cationic antiseptic. Alternatively, for certain of these embodiments, the moisturizer or substantive moisturizer composition is applied before applying the cationic antiseptic. For certain of these embodiments, the moisturizer or substantive moisturizer composition and the multi-valent cationic antiseptic are applied within 12 hours of each other. For certain of these embodiments, the moisturizer or substantive moisturizer composition and the multi-valent cationic antiseptic are applied within 4 hours of each other. For certain of these embodiments, preferably the moisturizer or substantive moisturizer composition and the multi-valent cationic antiseptic are applied within less than 120, 60, or 30 minutes of each other. For certain of these embodiments, the moisturizer or substantive moisturizer composition is applied at the same time as applying the multi-valent cationic antiseptic. For certain of these embodiments the moisturizer or substantive moisturizer composition contains the multi-valent cationic antiseptic, and the moisturizer and antiseptic are applied simultaneously.

Certain commercially available mouth moisturizing products used to treat ventilated patients have been found to include components that have film-forming properties and often leave behind a peelable, unabsorbed film as the product dries on the tissue upon which it is applied. This is particularly problematic for mouth moisturizers used in a hospital setting on ventilated patients, where mouth moisturizers are used both inside of the patient's mouth and on the lips. It has been found that as such moisturizers dry and are re-applied, a buildup of residue can give the appearance of dried, peeling lips. This can give an appearance or impression, for example, to hospital visitors, that patients are not properly cared for. Furthermore, once the film cracks and peels the moisturization "barrier" can be lost.

It has also now been found that such moisturizers shrink to a considerable extent when dried. Shrinkage is believed to contribute to the undesirable appearance. For certain embodiments, including any one of the above embodiments of the method and kit, levels and combinations of multi-valent cationic antiseptic-compatible thickeners, humectants, and excipients are combined such that peel-able film formation by the moisturizer or substantive moisturizer composition is minimized and the product is more esthetically pleasing when dried on oral tissue, such as the lips. For certain of these embodiments, the moisturizer or substantive moisturizer composition has a shrinkage of less than 10 percent when dried under ambient conditions for 2 hours. For certain embodiments, ambient conditions include 22-25° C. and 30 to 50 percent relative humidity. For certain embodiments, ambient conditions include 25° C. and 30 percent relative humidity. Shrinkage is easily determined by coating a substrate of known area, allowing the composition to dry and measuring the area of the dried composition, for example, according to Test Method D. A dried film of at least 50 microns and preferably not more than 350 microns in thickness may be used. Shrinkage measurements should be done on a surface that allows the composition to debond if it is inclined to do so upon drying. This typically means it should be done on the lowest surface energy substrate that allows one to put down a uniform coating without dewetting.

For certain of these embodiments, the moisturizer or substantive moisturizer composition when dried on a surface, such as the surface of a clear plastic petri dish, does not form a self-supporting film, that is, it cannot be peeled from the surface in a single piece. For certain of these embodiments, the dried moisturizer or substantive moisturizer composition cannot be peeled from the surface in a piece having a size greater than 30 percent of the area of the dried moisturizer or substantive moisturizer composition. For certain embodiments, self-supporting means that when the composition is dried on a suitable surface such as a release liner of suitably low surface energy, a film so formed can be removed from the release liner in a single piece and the film is capable of supporting its own weight. Evaluation for such characteristics may be carried out using Test Method D described below. Sufficient coating is typically applied to ensure a dried film of at least 50 microns and preferably not more than 350 microns in thickness.

The moisturizer or substantive moisturizer composition is applied in an amount sufficient to cover oral tissue that is susceptible to becoming excessively dry and compromised. For certain embodiments, including any one of the above method embodiments, the moisturizer or substantive moisturizer is applied in an amount of 1 to 10 grams per application. More may be applied if any excess is removed.

As indicated above, such oral tissue includes, for example, lips, mucosal tissue, tongue, and teeth. For certain embodiments, including any one of the above embodiments, the oral tissue is oral mucosal tissue. For certain of these embodiments, the oral mucosal tissue is selected from the group consisting gingiva, buccal mucosa, the floor of the mouth, the hard palate, the soft palate, the dorsal tongue, the lateral tongue, the ventral tongue, an oropharyngeal surface, and combinations thereof.

Subjects who may benefit from the present methods include any who have a condition of dry oral tissue. However, mechanically ventilated patients, such as those in a hospital setting, may receive significantly improved care. For certain embodiments, including any one of the above method embodiments, the subject is a patient in an Intensive Care Unit. For certain of these embodiments, the subject is a mechanically ventilated patient.

For certain embodiments of the oral care kit, including of any one of the above kit embodiments, the oral care kit includes at least one dose of the multi-valent cationic antiseptic composition. One dose is an amount sufficient for application to cover at least a portion of the oral tissue of a subject, preferably all of the oral mucosal tissue of a subject. For certain embodiments, one dose is 1 to 15 mL of the antiseptic composition. For certain of these embodiments, the kit includes at least 15 mL of the multi-valent cationic antiseptic composition. For certain of these embodiments, the kit includes at least 30 mL of the multi-valent cationic antiseptic composition. For certain of these embodiments, the kit includes at least two 15 mL unit dose containers of the multi-valent cationic antiseptic composition. Although the amounts are expressed in mL units, these amounts are understood to include their mass equivalents. For example, 1 mL of the multi-valent antiseptic composition is equivalent to an amount of 0.9 to 1.1 grams, depending upon the particular formulation density. In the case of the composition being in the form of a foam, the amount in grams may be less than this.

For certain embodiments, the oral care kit includes the moisturizer or substantive moisturizing composition supplied in an amount sufficient to cover at least a portion of the oral tissue of a subject, preferably all of the oral mucosal tissue of a subject, more preferably also including the lips. For certain of these embodiments, the moisturizer or substantive moisturizing composition is supplied in an amount sufficient for at least one application to the oral tissue of the subject at 1 to 10 grams per application. For certain of these embodiments, the moisturizer or substantive moisturizing composition is supplied in an amount sufficient for at least 4 applications to the oral tissue of the subject at 1 to 10 grams per application. For certain of these embodiments, the moisturizer or substantive moisturizing composition is supplied in at least 4 unit dose packages of 1 to 10 grams per package.

Significantly improved flexibility is provided by the oral care kit for applying the moisturizer composition whenever a subject is in need of an additional application. For example, some patients have significantly drier mouths than others and may benefit from more frequent applications of the moisturizer or substantive moisturizer composition. For certain embodiments, including any one of the above oral care kit embodiments, preferably the moisturizer or substantive moisturizing composition is supplied in a single container. For certain of these embodiments, the amount of moisturizer or substantive moisturizing composition supplied in the single container is an amount sufficient for at least 4 separate applications to all of the oral mucosal tissue and lips of a subject.

As indicated above, the moisturizer or substantive moisturizer composition and the multi-valent cationic antiseptic may, in certain embodiments, be applied at the same time. This may be carried out by applying the moisturizer immediately before or after application of the antiseptic. However, for certain embodiments, including any one of the above embodiments where the moisturizer and antiseptic are applied at the same time, preferably the moisturizer or substantive moisturizer composition comprises a solution of the multi-valent cationic antiseptic.

Subjects who are unable to clean their oral tissue, such as ventilated patients, are in need of periodic oral tissue cleaning. This can be carried out using a de-briding composition, such as a hydrogen peroxide composition. Oral debriding refers to removal of plaque and calculus from the teeth but also may assist in breaking down thick mucous in the oral cavity that is otherwise difficult to remove. For certain embodiments, including any one of the above method embodiments, the method further comprises applying a de-briding composition comprising hydrogen peroxide. For certain embodiments, including any one of the above oral care kit embodiments, the kit further comprises a de-briding composition, which in one embodiment comprises hydrogen peroxide. For certain of these embodiments, the hydrogen peroxide is stabilized. In certain embodiments, the hydrogen peroxide includes a stabilizing component which maintains the de-briding composition at a pH of 2.5 to 4, preferably 2.8 to 3.8, and wherein the de-briding composition essentially excludes any component which causes a precipitate when combined with a multi-valent cationic antiseptic used in the multi-valent cationic antiseptic composition when tested according to Test Method F. For certain of these embodiments, the hydrogen peroxide is stabilized with a buffer component selected from the group consisting of buffers such as monovalent alkyl carboxylic acids and alkyl phosphoric acids wherein the alkyl group optionally comprises a carbon chain substituted with or interrupted by one or more N, O, or S atoms; polyalkoxylated derivatives such as phosphate or carboxylate terminated polyethoxylated and/or propoxylated alkyl alcohols; alpha-hydroxy acids such as lactic acid, gluconic acid, citric acid (when used at a pH where only one acid group is ionized); amino acids; phosphoric acid; and boric acid. Such buffer components are selected and used at concentrations such that a precipitate is not formed when the buffer component is combined with the multi-valent cationic antiseptic. This can be determined according to Test Method F. Preferred acids have only substantially a single acid group at least partially ionized at pH 3.5. For example, phosphoric acid is useful since it has pKa values of 2.15, 7.2, and 12.35. Thus, at pH 3.5 there is predominantly a single ionized group. Preferably, the buffer has a pKa less than 3.5, and if it comprises a second acid functionality the second pKa is greater than 4.5 as determined by standard potentiometric titration.

For certain of these embodiments, the de-briding composition is supplied in an amount sufficient for at least one application to the oral tissue of the subject. For certain of these embodiments, the de-briding composition is supplied in at least 4 unit dose containers, each containing an amount sufficient for a single application to the oral tissue of the subject. For certain of these embodiments, the de-briding composition is supplied in a single container in an amount sufficient for at least 4 applications to the oral tissue of the subject.

For certain embodiments, including any one of the above method and oral care kit embodiments which include a de-briding composition, the de-briding composition further includes a sweetener selected from the group consisting of sucralose, aspartame, sugars and sugar alcohols including but not limited to xylose, sucrose, maltose, mannose, glucose, xylitol, sorbitol, mannitol, erythritol, maltitol, lactitol, and a combination thereof Additional compositions may be supplied by the oral care kit. For certain embodiments, including any one of the above kit embodiments, the oral care kit further comprises an additional oral care composition selected from the group consisting of an oral rinse, a toothpaste, a lip care composition, a mouth care composition, and combinations thereof. A mouth care composition may include an analgesic, wound healing paste, tooth care composition, or other oral composition.

As indicated above, the compositions supplied by the oral care kit may be applied with various application means. The oral care kit provides a significant advance in flexibility of applying the above described composition by supplying a plurality of applicator tools and in a manner which shows compliance to a treatment protocol. Accordingly, for certain embodiments, including any one of the above kit embodiments, the oral care kit further comprises a plurality of applicator tools for applying at least one composition to the oral tissue of a subject. For certain of these embodiments, the plurality of applicator tools is selected from the group consisting of swabs, suction swabs, toothbrushes, suction toothbrushes, and combinations thereof. For certain of these embodiments, at least a portion of the plurality of applicator tools is packaged so that usage of the at least a portion of the plurality of applicator tools shows compliance with at least a portion of a protocol for treating the oral tissue of a subject. For example, removal of a tool from a particular section of the kit indicates that an application of a particular composition was carried out within a particular time frame. For certain of these embodiments, the at least a portion of the plurality of applicator tools is packaged with an indication of at least one time frame for applying at least one composition comprising the kit. For certain of these embodiments, the indication is a color code, a symbol, a picture, or a printed number.

For certain embodiments, including any one of the above embodiments of the kit including a plurality of applicator tools, the oral care kit comprises a plurality of packages, wherein each package contains at least one kit component selected from the group consisting of an applicator tool, a suction yankaeur, a suction catheter, a Y-connector, a vacuum adapter handle, a multi-valent cationic antiseptic composition, a moisturizer or substantive moisturizing composition, a de-briding composition, other mouth care products, and a combination thereof. For certain of these embodiments, the package is a bag, a box, a tray, or a combination thereof.

For certain embodiments, including any one of the above kit embodiments, the kit comprises a kit package comprising a plurality of pockets, each pocket containing at least one component of the oral care kit. Referring to FIG. 1, a perspective view of one embodiment of an oral care kit 10 described herein for use in treating a ventilated patient is illustrated. Oral care kit 10 includes a kit package 20 which comprises a plurality of pockets 30. Pockets 30 may be sized the same or one or more of the plurality of pockets may be sized differently than the other pockets, such as illustrated by low pocket 35. Oral care kit 10 is illustrated with extension flap 40, which may include an opening or cut-out (not shown) for hanging oral care kit 10 on a hook or other hanger means at a location convenient for use in treating a patient, for example, near the patient's bed. Alternatively, oral care kit 10 may be simply set upon a surface, in which case flap 40 need not be used or even present.

For certain embodiments, each pocket comprising the kit package 20 is sized to accommodate at least one kit component to be held within the pocket. For example, each of pockets 30 may be sized to hold at least one applicator tool package 60. For certain embodiments, preferably each of pockets 30 holds a sufficient number of applicator tool packages 60 so that all applications of the compositions described above and as required by a treatment protocol can be applied within a specified time period according to the protocol using applicator tools contained within applicator tool packages 60 held within a particular pocket designated for the specified time period. For example, for certain embodiments, oral care kit 10 provides for a treatment protocol covering a specified time period, and pockets 31, 32, and 33 are each designated for a separate application time segment within the specified time period. For certain embodiments, oral care kit 10 provides for a 24 hour treatment protocol, and pockets 31, 32, and 33 are each designated for separate application times, for example, at 0 and 12 hours, at 4 and 16 hours, and at 8 and 20 hours, respectively. Alternative specified time periods, such as 12 hours, 36 hours, 48 hours, and the like may be used. Moreover, alternative application times may be provided, such as at 2 hours, 6 hours, 10 hours, and the like. For example, pockets 31, 32, and 33 may be designated for separate application times at 0, 6, 12, and 18 hours; 2, 8, 14, and 20 hours; and 4, 10, 16, and 22 hours, respectively. In addition, one or more additional pockets or other receptacles may be included in the oral care kit to supply additional applicator tools for additional applications of the moisturizer or substantive moisturizing composition, the de-briding composition, and/or other oral care compositions as needed by the patient. Compliance with a treatment protocol can be shown or is evident by usage of applicator tools contained within applicator tool packages 60 held within each of pockets 31, 32, and 33. For example, usage of all of the applicator tool packages 60 in pockets 31, 32, and 33 may show compliance with a 24 hour treatment protocol.

FIG. 1 illustrates at least one applicator tool package 60 to be held within each of pockets 30. Applicator tool packages 60 each contain at least one applicator tool. For certain embodiments, the at least one applicator tool is selected from the group consisting of swabs, suction swabs, toothbrushes, suction toothbrushes, and combinations thereof. For certain of these embodiments, the at least one applicator tool is a suction swab. Applicator tool packages 60 may be a molded tray as illustrated in FIG. 1. However, a box, a bag, or other packaging and/or protective means may be used. For certain embodiments, preferably at least a portion of applicator tool packages 60 is sufficiently transparent to allow visually viewing and identifying the contents of applicator tool packages 60, without opening these packages.

Low pocket 35 illustrated in FIG. 1 holds various compositions supplied with oral care kit 10. Moisturizer or substantive moisturizer composition container 70 is positioned within sub-pocket 36, which in turn is contained within low pocket 35. Low pocket 35 may also hold additional oral care composition containers, such as multi-valent cationic antiseptic composition containers, de-briding composition containers, and the like. For certain embodiments, preferably low pocket 35 holds at least one moisturizer or substantive moisturizer composition container 70, at least one multi-valent cationic antiseptic composition container (not shown in FIG. 1), and at least one de-briding composition container 80. For certain embodiments, all compositions held by low pocket 35 can be visually observed simply by looking into low pocket 35.

Figure 2:
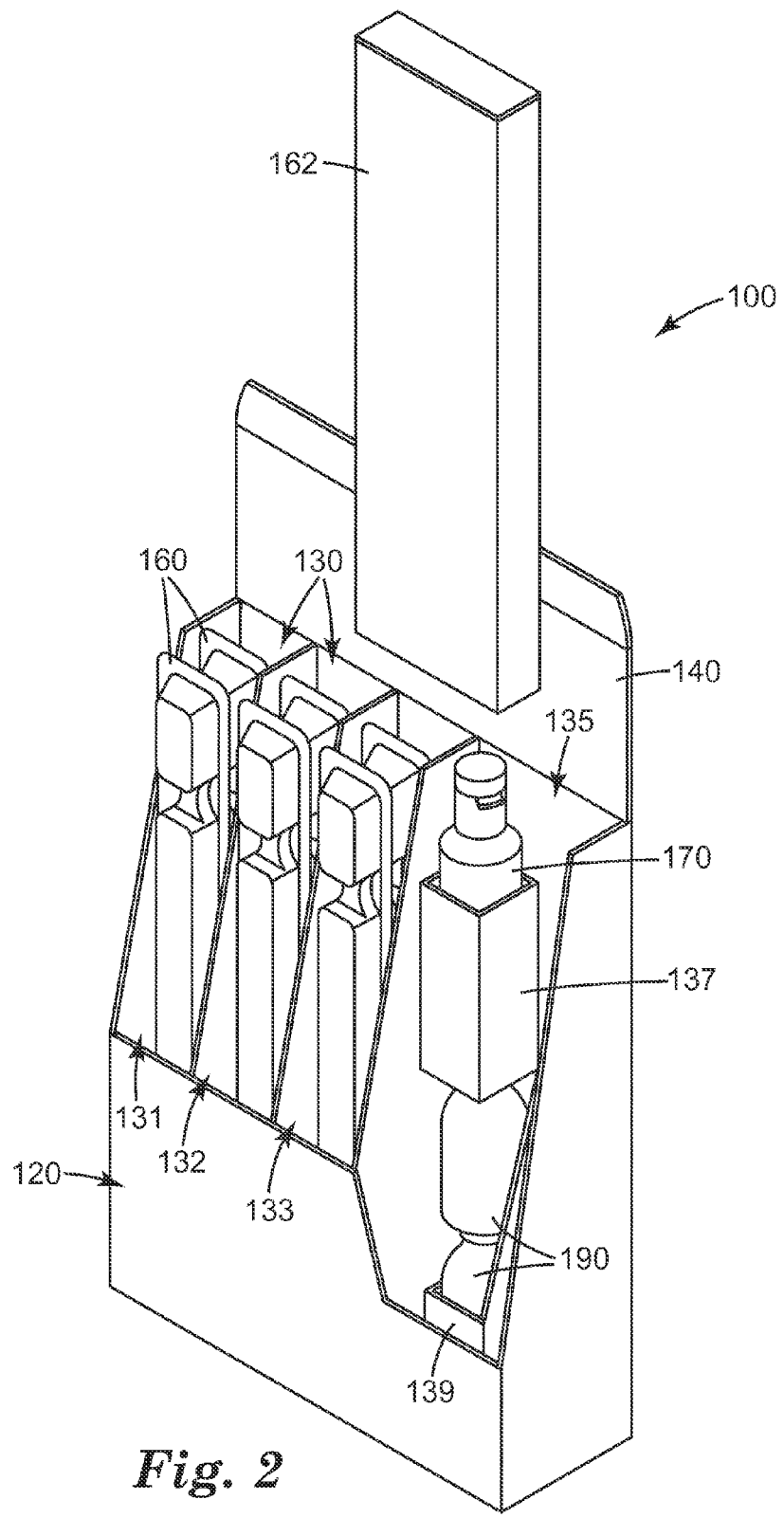
FIG. 2 is a perspective and partially exploded view of an oral care kit according to the present invention.

Referring to FIG. 2, a perspective view of oral care kit 100 for use in treating a mechanically ventilated patient is illustrated. Oral care kit 100 includes a kit package 120 which comprises a plurality of pockets 130, as described above for pockets 30 in FIG. 1. Each of pockets 130 contains two applicator tool packages 160. Applicator tool packages 160 are as described above for applicator tool packages 60 in FIG. 1. Oral care kit 100 is illustrated with extension flap 140, as described above for extension flap 40 in FIG. 1.

For certain embodiments, oral care kit 100 provides for a treatment protocol covering a specified time period, and pockets 131, 132, and 133 are each designated for separate application times within the specified time period. For certain embodiments, oral care kit 100 provides for a 24 hour treatment protocol, and pockets 131, 132, and 133 are designated for separate application times, for example, 0 and 12 hours, 4 and 16 hours, and 8 and 20 hours, respectively. Alternative specified time periods, such as 12 hours, 36 hours, 48 hours, and the like may be used. Moreover, alternative application times may be provided, as discussed above for FIG. 1. In addition, one or more additional pockets or other receptacles may be included in oral care kit 100 to supply additional applicator tools for additional applications of the moisturizer or substantive moisturizer composition, the de-briding composition, and/or other oral care compositions as needed by the patient or as required by a treatment protocol. Compliance with a treatment protocol can be shown or is evident by usage of applicator tools contained within applicator tool packages 160 held within each of pockets 131, 132, and 133. For example, usage of all of the applicator tool packages 160 in pocket 131 may show compliance with applications required by a treatment protocol at 0 and 12 hours; or usage of all of the applicator tool packages 160 in pockets 131, 132, and 133 may show compliance with an entire 24 hour treatment protocol.

Low pocket 135 illustrated in FIG. 2 holds various compositions supplied with oral care kit 100. Moisturizer or substantive moisturizer composition container 170 is positioned within sub-pocket 137, which in turn is contained within low pocket 135. Low pocket 135 also holds multi-valent cationic antiseptic composition containers 190 within sub-pocket 139. Low pocket 135 also holds at least one de-briding composition container (not shown). Additional oral care compositions (not shown) may be held within low pocket 135 or elsewhere within oral care kit 100, for example, in an additional pocket (not shown).

Low pocket 135 also holds auxiliary package 162 for containing additional suction components for use in conjunction with suction applicator tools. For example, auxiliary package 162 may contain at least one of a suction yankaeur, a suction catheter, a Y-connector, a vacuum adapter handle, or a combination thereof. Auxiliary package 162 may be a box as illustrated in FIG. 2 or alternatively may be a molded tray, a bag, or the like, preferably a box or bag. At least a portion of auxiliary package 162 may be sufficiently transparent to allow visual observation of the components contained therein. In an alternative embodiment, oral care kit 100 includes an additional pocket (not shown) for holding auxiliary package 162.

Figure 3:
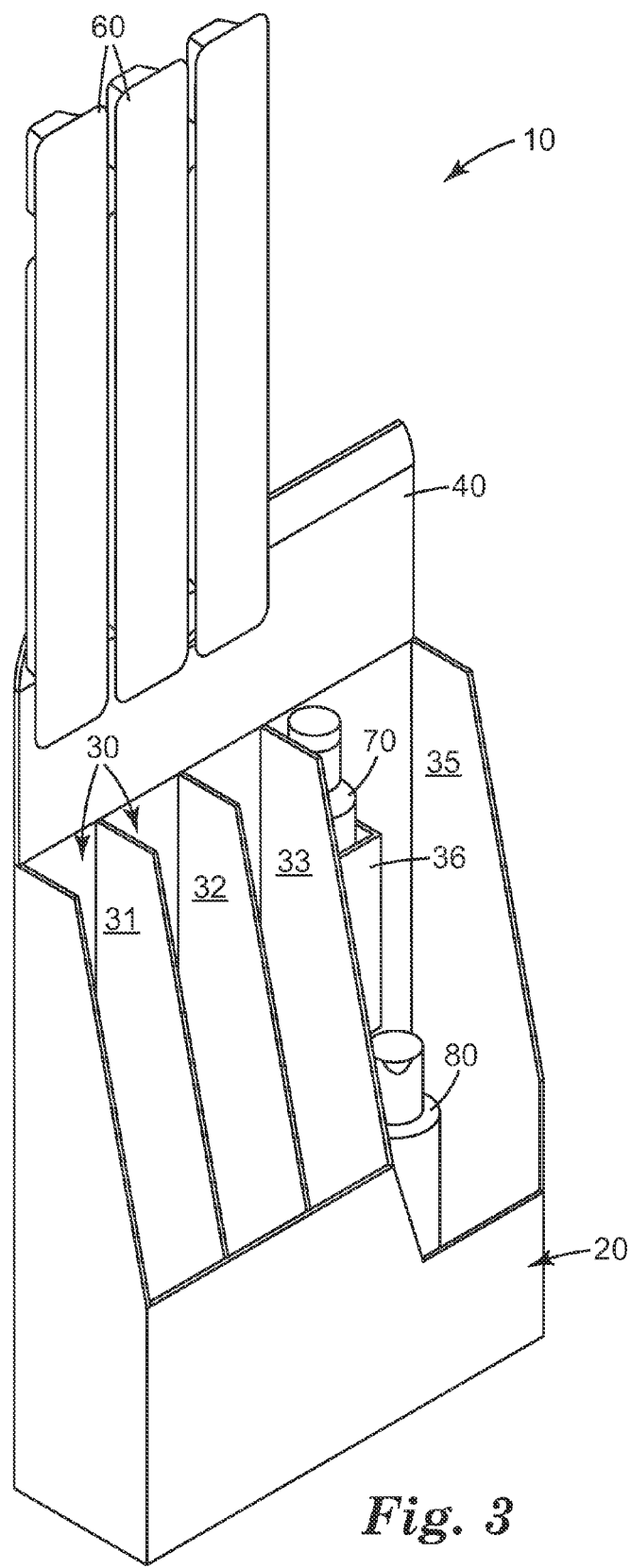
FIG. 3 is a perspective and partially exploded view of an oral care kit according to the present invention.
Figure 4:
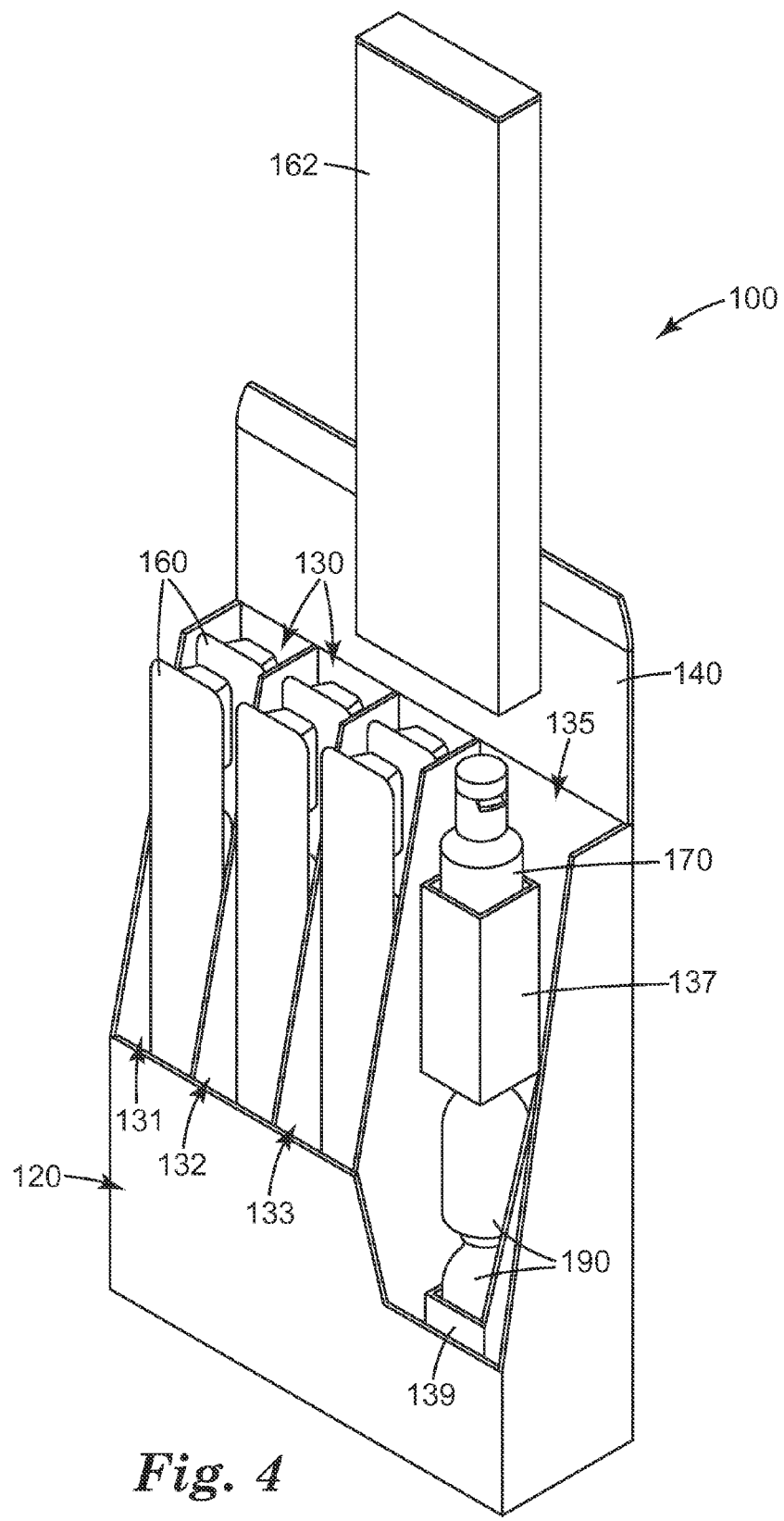
FIG. 4 is a perspective and partially exploded view of an oral care kit according to the present invention.

FIGS. 3 and 4 are identical to FIGS. 1 and 2, except that applicator tool packages 60 and 160, respectively, have been rotated 180 degrees. In such embodiments, the user can view any printing or other graphics on the now exposed flat sides of applicator tool packages 60 and 160 without rotating these packages.

For certain embodiments, including any one of the above method or oral care kit embodiments which include a moisturizer composition, the moisturizer composition is preferably a substantive moisturizer composition.

The moisturizer or substantive moisturizer composition as well as compositions comprising the multi-valent cationic antiseptic described above may include at least one additional component selected from the group consisting of enhancers, surfactants, hydrophilic compounds, hydrophobic compounds, and combinations thereof.

Enhancer Component:

Compositions included in the present method and kit may include an enhancer to enhance the antimicrobial activity. The activity enhancement may be especially useful against Gram negative bacteria, such as *E. coli* and *Psuedomonas* sp. The enhancer chosen preferably affects the cell envelope of the bacteria. While not bound by theory, it is presently believed that the enhancer functions by allowing the antiseptic to more easily enter the cell cytoplasm and/or by facilitating disruption of the cell envelope. The enhancer component may include a phenolic compound (such as certain antioxidants and parabens), a (C1-C10)monohydroxy alcohol, or a glycol ether (i.e., ether glycol). Various combinations of enhancers can be used if desired.

In some embodiments, other enhancers may be useful, such as the siderophores and iron-bonding proteins described in U.S. Ser. No. 10/936,949, filed Sep. 8, 2004 entitled "Antimicrobial Compositions and Methods", if they are formulated such that there is minimal or no interaction between the multivalent cationic antiseptic and the siderophore or iron-binding protein; and the sugar and/or alcohols as described in U.S. Ser. No. 60/660,830, filed Mar. 10, 2005 entitled "Methods of Reducing Microbial Contamination."

One or more enhancers may be used in the compositions included in the present method and kit at a suitable level to produce the desired result. For certain embodiments, they are present in a total amount greater than 0.01 wt-%, preferably in an amount greater than 0.1 wt %, more preferably in an amount greater than 0.2 wt %, even more preferably in an amount greater than 0.25 wt % and most preferably in an amount greater than about 0.4 wt % based on the total weight of the ready to use composition. In a preferred embodiment, they are present in a total amount of no greater than 20 wt-%, based on the total weight of the ready to use composition. Such concentrations typically apply to phenolics, ether glycols, and (C5-C10)monohydroxy alcohols. Generally, higher concentrations are needed for (C1-C4)monohydroxy alcohols, as described in greater detail below. The total concentration of the enhancer component relative to the total concentration of the antiseptic component is preferably within a range of 10:1 to 1:300 on a weight basis.

An additional consideration when using an enhancer is the solubility and physical stability in the compositions. Many of the enhancers discussed herein are insoluble in hydrophobic components such as hydrophobic esters, mineral oil, and petrolatum. It has been found that the addition of a minor amount (typically less than 30 wt-%, preferably less than 20 wt-%, and more preferably less than 12 wt-%) of a hydrophilic component not only helps dissolve and physically stabilize the composition but improves the antimicrobial activity as well. Alternatively, the enhancer may be present in excess of the solubility limit provided that the composition is physically stable. This may be achieved by utilizing a sufficiently viscous composition that stratification (e.g. settling or creaming) of the antiseptic does not appreciably occur.

A phenolic compound enhancer is typically a compound having the following general structure (including at least one group bonded to the ring through an oxygen:

wherein: o is 0 to 3 (especially 1 to 3), m is 1 to 3 (especially 1 to 2), each $R^5$ independently is alkyl or alkenyl of up to 12 carbon atoms (especially up to 8 carbon atoms) optionally substituted with O in or on the chain (e.g., as a carbonyl group) or OH on the chain, and each $R^6$ independently is H or alkyl or alkenyl of up to 8 carbon atoms (especially up to 6 carbon atoms) optionally substituted with O in or on the chain (e.g., as a carbonyl group) or OH on the chain, but where $R^6$ is H, o preferably is 1 or 2.

Examples of phenolic enhancers include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, 2-phenoxyethanol, as well as combinations thereof. A preferred group of the phenolic derivative compounds is the phenol species having the general structure shown above where $R^6$=H and where $R^5$ is alkyl or alkenyl of up to 8 carbon atoms, and o is 1, 2, or 3, especially where at least one $R^5$ is butyl and particularly tert-butyl, and especially the non-toxic members thereof. Some of the preferred phenolic derivative enhancers are BHA, BHT, methyl paraben, ethyl paraben, propyl paraben, and butyl paraben as well as combinations of these.

One or more phenolic derivative compounds may be used in the compositions included in the present method and kit at a suitable level to produce the desired result. The concentrations of the phenolic compounds in medical-grade compositions may vary widely, but as little as 0.001 wt-%, based on the total weight of the composition, can be effective when the above-described esters are present within the above-noted ranges. In certain embodiments, they are present in a total amount of at least 0.01 wt-%, more preferably at least 0.10 wt-%, and even more preferably at least 0.25 wt-%, based on the ready to use composition. In a preferred embodiment, they are present in a total amount of no greater than 8 wt-%, more preferably no greater than 4 wt-%, and even more preferably no greater than 2 wt-%, based on the ready to use composition. It is preferred that the ratio of the total phenolic concentration to the total concentration of the antiseptic component be within a range of 10:1 to 1:300 on a weight basis.

The above-noted concentrations of the phenolic derivative enhancers are normally observed unless concentrated formulations for subsequent dilution are intended. On the other hand, the minimum concentration of the phenolics and the antiseptic to provide an antimicrobial effect will vary with the particular application.

(C1-C10) Monohydroxy alcohol enhancers include the lower (i.e., C1-C4) monohydroxy alcohols (e.g., methanol, ethanol, isopropanol, and butanol) as well as longer chain (i.e., C5-C10) monohydroxy alcohols (e.g., isobutanol, t-butanol, octanol, and decanol). In certain preferred embodiments, the alcohols useful in the compositions included in the present method and kit are selected from the group consisting of methanol, ethanol, isopropyl alcohol, and mixtures thereof.

One or more alcohols may be used in the compositions included in the present method and kit at a suitable level to produce the desired result. In one embodiment, the short chain (i.e., C1-C4) alcohols are present in a total amount of at least 5 wt-%, even more preferably at least 10 wt-%, even more preferably at least 15 wt-%, and even more preferably at least 20 wt-%, based on the total weight of the ready to use composition. In a preferred embodiment, the (C1-C4)alcohols are present in a total amount of no greater than 50 wt-%, more preferably no greater than 40 wt-%, and even more preferably no greater than 30 wt-%, based on the total weight of the ready to use composition.

For certain applications, lower alcohols may not be preferred due to the strong odor and potential for stinging and irritation. This can occur especially at higher levels. In applications where stinging or burning is a concern, the concentration of (C1-C4)alcohols is preferably less than 20%, more preferably less than about 15%.

In certain embodiments, longer chain (i.e., C5-C10) alcohols are present in a total amount of at least 0.1 wt-%, more preferably at least 0.25 wt-%, and even more preferably at least 0.5 wt-%, and most preferably at least 1.0%, based on the ready to use composition. In a preferred embodiment, the (C5-C10)alcohols are present in a total amount of no greater than 10 wt-%, more preferably no greater than 5 wt-%, and even more preferably no greater than 2 wt-%, based on the total weight of the ready to use composition.

Ether glycol enhancers include those of the formula:

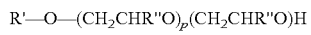

wherein R'=H, a (C1-C8)alkyl, a (C6-C12) aryl or a (C6-C12) aralkyl or (C6-C12) alkaryl; and each R" is independently=H, methyl, or ethyl; and p=0-5, preferably 1-3. Examples include 2-phenoxyethanol, dipropylene glycol, triethylene glycol, the line of products available under the trade designation DOWANOL DB (di(ethylene glycol) butyl ether), DOWANOL DPM (di(propylene glycol)monomethyl ether), and DOWANOL TPnB (tri(propylene glycol) monobutyl ether), as well as many others available from Dow Chemical, Midland Mich. Some of these compounds are not suitable for use in the oral environment but may be useful on other mucosal tissues.

One or more ether glycols may be used in the compositions included in the present method and kit at a suitable level to produce the desired result. In a preferred embodiment, they are present in a total amount of at least 0.01 wt-%, based on the total weight of the ready to use composition. In a preferred embodiment, they are present in a total amount of no greater than 20 wt-%, based on the total weight of the ready to use composition.

Surfactants:

Compositions included in the present method and kit may include one or more surfactants to emulsify the composition and to help the composition wet the surface and/or to aid in contacting the microorganisms. As used herein the term "surfactant" means an amphiphile (a molecule possessing both polar and nonpolar regions which are covalently bound) capable of reducing the surface tension of water and/or the interfacial tension between water and an immiscible liquid. The surfactant can be cationic, nonionic, or amphoteric. Combinations of surfactants can be used if desired.

In certain embodiments, preferably the surfactants useful in the compositions included in the present method and kit are selected from the group consisting of certain poloxamer (polyethylene oxide/polypropylene oxide block copolymers) surfactants, cationic surfactants, zwitterionic surfactants, and mixtures thereof. Cationic, amphoteric, and non-ionic surfactants and in particular certain ethylene oxide/propylene oxide surfactants such as poloxamers are preferred.

One or more surfactants may be used in the compositions included in the present method and kit at a suitable level to produce the desired result. In certain embodiments, they are present in a total amount of at least 0.01 wt-%, preferably 0.1 wt %, more preferably at least 0.5 wt-%, and even more preferably at least 1.0 wt-%, based on the total weight of the ready to use composition. In certain embodiments where, for example, irritation may be a concern, they are present in a total amount of no greater than 10 wt-%, more preferably no greater than 5 wt-%, and even more preferably no greater than 2 wt-%, based on the total weight of the ready to use composition. The ratio of the total concentration of surfactant to the total concentration of the antiseptic is preferably within a range of 5:1 to 1:100.

Exemplary cationic surfactants include, but are not limited to, salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium, or alkylpyridinium having compatible anionic counterions such as halides (preferably chlorides or bromides) or alkyl sulfates such as methosulfate or ethosulfate as well as other anionic counterions; imidazoline derivatives; amine oxides of a cationic nature (e.g., at an acidic pH), and mixtures thereof.

In certain preferred embodiments, the cationic surfactants useful in the present methods and kits are selected from the group consisting of tetralkyl ammonium, trialkylbenzylammonium, and alkylpyridinium halides, and mixtures thereof.

Also particularly preferred are amine oxide surfactants including alkyl and alkylamidoalkyldialkylamine oxides of the following formula:

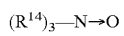

wherein $R^{14}$ is a (C1-C30)alkyl group (preferably a (C1-C14) alkyl group) or a (C6-C18)aralkyl or alkaryl group, wherein any of these groups can be optionally substituted in or on the chain by N-, O-, or S-containing groups such as amide, ester, hydroxyl, and the like. Each $R^{14}$ may be the same or different provided at least one $R^{14}$ group includes at least eight carbons. Optionally, the $R^{14}$ groups can be joined to form a heterocyclic ring with the nitrogen to form surfactants such as amine oxides of alkyl morpholine, alkyl piperazine, and the like. Preferably two $R^{14}$ groups are methyl and one $R^{14}$ group is a (C12-C16)alkyl or alkylamidopropyl group. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company of Northfield, Ill.

Amphoteric surfactants include those having tertiary amine groups, which may be protonated, as well as quaternary amine containing zwitterionic surfactants. Examples include:

Ammonium carboxylate amphoterics, which can be represented by the following formula:

$$R^{17}-(C(O)-NH)_a-R^{18}-N^+(R^{19})_2-R^{20}-COO^-$$

wherein: a=0 or 1; $R^{17}$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^{17}$ may be optionally substituted with one or more N, O, or S atoms, or one or more hydroxyl, carboxyl, amide, or amine groups; $R^{19}$ is H or a (C1-C8)alkyl group (saturated straight, branched, or cyclic group), wherein $R^{19}$ may be optionally substituted with one or more N, O, or S atoms, or one or more hydroxyl, carboxyl, amine groups, a (C6-C9)aryl group, or a (C6-C9)aralkyl or alkaryl group; and $R^{18}$ and $R^{20}$ are each independently a (C1-C10)alkylene group that may be the same or different and may be optionally substituted with one or more N, O, or S atoms, or one or more hydroxyl or amine groups.

More preferably, in the formula above, $R^{17}$ is a (C1-C18) alkyl group, $R^{19}$ is a (C1-C2)alkyl group preferably substituted with a methyl or benzyl group and most preferably with a methyl group. When $R^{19}$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

Ammonium sulfonate amphoteric surfactants are often referred to as "sultaines" or "sulfobetaines" and can be represented by the following formula $$R^{17}-(C(O)-NH)_n-R^{18}-N^+(R^{19})_2-R^{20}SO_3^-$$

wherein $R^{17}$-$R^{20}$ and "a" are defined above. Examples include cocamidopropylhydroxysultaine (commercially available as MACKAM 50-SB from McIntyre Group Ltd.). The sulfoamphoterics may be preferred over the carboxylate amphoterics since the sulfonate group will remain ionized at much lower pH values.

Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy) ethanol available under the trade name NONIDET P-40, both from Sigma, St. Louis, Mo.), ethoxylated and/or propoxylated aliphatic alcohols (e.g., that available under the trade name Brij from ICI), ethoxylated glycerides, ethoxylated/propoxylated block copolymers such as the Pluronic and Tetronic surfactants available from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from 3M Company, St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In certain preferred embodiments, the nonionic surfactants useful in the compositions of the present invention are selected from the group consisting of Poloxamers such as PLURONIC from BASF, sorbitan fatty acid esters, and mixtures thereof.

Hydrophilic Component:

Compositions of the present methods and kits can include a hydrophilic or water-soluble component to help solubilize and/or physically stabilize the antiseptic and/or enhancer component in the composition and/or to enhance the antimicrobial efficacy and/or the speed of antimicrobial efficacy. The incorporation of a sufficient amount of hydrophilic component in hydrophobic ointments for use in applications such as lip care compositions results in compositions with significantly better antimicrobial activity both in terms of speed of kill and extent of kill. While not intended to be bound by theory it is believed that the incorporation of the hydrophilic component allows more antiseptic to be available at the surface or to more rapidly diffuse to the surface of the ointment during use. Certain compositions may be solutions, emulsions (one liquid/gel/paste dispersed in another liquid/gel/paste), or dispersions (solid in liquid/paste/gel). In general, for improved antimicrobial activity the ratio of total hydrophilic component to total hydrophobic component (water insoluble ingredients) should be at least 5:95 wt/wt, preferably at least 10:90 wt/wt, more preferably at least 15:85 wt/wt and most preferably at least 20:80 wt/wt. Levels as high as 30:70, 40:60, 50:50 wt/wt of total hydrophilic component to total hydrophobic component (water insoluble ingredients) or higher may be appropriate for certain compositions.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limit above), N-methylpyrrolidone, alkyl esters (i.e., having a sufficiently small number of carbon atoms to meet the solubility limit above), and the lower monohydroxy alcohols discussed above as enhancers, as well as combinations thereof. Thus, a lower monohydroxy alcohol can function as both a hydrophilic compound and an enhancer. Preferably, the hydrophilic components include polyhydric alcohols, lower alkyl ethers, and short chain esters. More preferably, the hydrophilic components include polyhydric alcohols.

Suitable polyhydric alcohols (i.e., organic compounds having more than one hydroxyl group) have a molecular weight of less than 500, preferably less than 400, and more preferably less than 200. Examples of polyhydric alcohols include, but are not limited to, glycerol, propylene glycol, dipropylene glycol, tripropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars (e.g., sucrose, glucose, fructose, mannose, xylose, saccharose, trehalose), sugar alcohols, and the like. Certain preferred polyhydric alcohols include glycols (i.e., those containing two hydroxyl groups) including glycerin and propylene glycol. Certain other preferred polyhydric alcohols include xylitol, mannitol, sorbitol, sucrose and polyglycerin.

Ethers include materials such as dimethylisosorbide, polyethylene glycol and methoxypolyethylene glycols, block and random copolymers of ethylene oxide and propylene oxide, and laureth-4. Alkyl esters include triacetin, methyl acetate, esters of polyethoxylated glycols, and combinations thereof.

In certain preferred embodiments, the hydrophilic components useful in the compositions of the present invention include those selected from the group consisting of glycols, and in particular glycerin, xylitol, and propylene glycol, and mixtures thereof.

If there are components in the composition that may esterify with hydroxylfunctional hydrophilic components conditions are selected to minimize this occurrence. For example, the components are not heated together for extended periods of time, the pH is maintained close to neutral if possible, and the like.

One or more hydrophilic materials may be used in the compositions of the present methods and kits at a suitable level to produce the desired result. In certain embodiments that also include a hydrophobic component as the component used in the greatest amount (which may be referred to as a "vehicle"), the hydrophilic component is present in a total amount of at least 0.1%, preferably at least 1 wt-%, more preferably at least 4 wt-%, and even more preferably at least 8 wt-%, based on the weight of the ready to use composition In certain embodiments, the hydrophilic component is present in a total amount of at least 10% by weight, at least 20% by weight, or at least 25% by weight. In certain embodiments, the hydrophilic component is present in a total amount of no greater than 70 wt-%, no greater than 60 wt-%, or no greater than 50 wt-%, based on the ready to use composition. When the hydrophilic component is present in the greatest amount it is referred to as a "vehicle."

For certain applications it may be desirable to formulate these antiseptics in compositions comprising a hydrophilic component vehicle that is thickened with soluble, swellable or insoluble (e.g. insoluble) organic polymeric thickeners or inorganic thickeners such as silica, fumed silica, precipitated silica, silica aerogel, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres such as those available under the tradenames "ZEOSPHERES" or "Z-LIGHT" from 3M. The above fillers can be used alone or in combination. Preferably, inorganic thickeners are compatible with the multi-valent cationic antiseptic. For certain embodiments, preferably the inorganic thickeners are very insoluble.

For certain embodiments, water can be used in significant amounts (e.g., at least 20 wt-%), and can even be the primary component, as long as the composition is highly viscous. Preferably, such highly viscous compositions have a viscosity of at least 20 cps, preferably, 50 centipoise (cps), more preferably at least 100 cps, even more preferably at least 1000 cps, even more preferably at least 2000 cps, even more preferably at least 5000 cps, even more preferably at least 7500 cps, even more preferably at least 10,000 cps, at least 25,000 cps, or as high as about 50,000 cps or 1,000,000 cps, or more. The viscosity can be measured as described below in the Viscosity Test. Most preferred compositions meet these viscosity values even after heating to 32 C.° or even 35 C.° or as high as 37 C.° to ensure when in contact with mammalian tissue the compositions remain substantive.

Hydrophobic Component:

Certain preferred compositions of the present methods and kits also include one or more hydrophobic materials. A hydrophobic material is typically an organic compound, which at 23° C. is a liquid, gelatinous, semisolid or solid and has a solubility in water of less than 5% by weight, preferably less than 1% by weight, more preferably less than 0.5% by weight, and even more preferably less than 0.1% by weight. These materials include compounds typically considered emollients in the cosmetic art.

Examples of general emollients include, but are not limited to, C6-C22 alkyl mono, di and tri esters of glycerin and propylene glycol, vegetable oils, short chain (i.e, C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12)aryl esters of (C4-C12)diacids or (C4-C12)diols optionally substituted in available positions by —OH; (C2-C18)alkyl or (C6-C12)aryl esters of glycerol, pentaerythritol, ethylene glycol, propylene glycol, as well as polyethoxylated derivatives of these; (C12-C22)alkyl esters or (C12-C22)ethers of polypropylene glycol; (C12-C22)alkyl esters or (C12-C22)ethers of polypropylene glycol/polyethylene glycol copolymer; and polyether polysiloxane copolymers. Additional examples of hydrophobic components include cyclic dimethicones including volatile cyclic silicones such as D3 and D4, polydialkylsiloxanes, polyaryl/alkylsiloxanes, silicone copolyols, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparafins (e.g. isooctane, isododecane, isooctadecane, etc.), squalene, and mineral oil, polysiloxane polyalkylene copolymers, dialkoxy dimethyl polysiloxanes; (C12-C22)alkyl and (C12-C22)alkenyl alcohols, and petroleum derived alkanes such as isoparafins, petrolatum, petrolatum USP, as well as refined natural oils (especially NF or USP grades) such as olive oil NF, cotton seed oil, peanut oil, corn oil, seasame oil, safflower oil, soybean oil, and the like, and blends thereof.

In certain preferred embodiments, the hydrophobic components useful in the compositions of the present methods and kits include those selected from the group consisting of vegetable oils, C6-C22 alkyl mono, di and tri esters of glycerin and propylene glycol, petrolatum USP and short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12)aryl esters of (C4-C12) diacids or (C4-C12)diols optionally substituted in available positions by —OH (such as diisopropyladipate, diisopropylsebacate); (C1-C9)alkyl or (C6-C12)aryl esters of glycerol, pentaerythritol, ethylene glycol, propylene glycol (such as glyceryl tricaprylate/caprate); and mixtures thereof. For certain embodiments, preferably the hydrophobic component is selected from one or more vegetable oils, C6-C22 alkyl mono, di and tri esters of glycerin and propylene glycol, and combinations thereof.

One or more hydrophobic materials may be used in the compositions of the present methods and kits at a suitable level to produce the desired result. In certain embodiments, the hydrophobic component is present in a total amount of at least 30 wt-%, preferably at least 50 wt-%, more preferably at least 60 wt-%, and even more preferably at least 70 wt-%, based on the ready to use composition. In certain of these embodiments, the hydrophobic component is present in a total amount of no greater than 99 wt-%, more preferably no greater than 95 wt-%, and even more preferably no greater than 92 wt-%, based on the ready to use composition. When the hydrophobic component is present in the greatest amount it is referred to as a "vehicle." If the hydrophobic component(s) and the hydrophilic component(s) are present at the same concentrations the continuous phase is consider the "vehicle". In other embodiments such as hydrophilic solutions and gels as well as emulsions, the composition may be for general use in the oral cavity. Where aspiration of the composition into the lung is concerned such as treatment of patients on mechanical ventilation it may be desirable to limit the amount of hydrophobic component in order to prevent lipoid pneumonia. In these applications the hydrophobic component may be present at less than 10 percent by weight of the composition or less than 5 percent or less than 3 percent or even less than 2 percent by weight of the composition. In certain embodiments the oral care composition may be essentially free of water insoluble or hydrophobic components.

Optional Additives:

Compositions of the present methods and kits may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anaesthetics, steroids, non-steorodial antinflammatory agents, or other anti-inflammatory agents), antiplaque, antigingivitis, or may contain materials useful in physically formulating various dosage forms of the present invention, such as excipients, flavors, vitamins, dyes, perfumes, fragrances, lubricants, thickening agents, stabilizers, tissue penetration enhancers, preservatives, or antioxidants.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

In those applications where emulsions are desirable, an emulsifier may be used. As used herein, an "emulsifier" means a small molecule or polymeric amphiphilic compound capable of helping to stabilize an emulsion when used alone or in combination with other emulsifiers or components. Emulsifiers used herein include many of the surfactants disclosed but may also include many other amphiphilic molecules. The emulsions are detectably more stable with the emulsifier present than without as determined by centrifugation and/or freeze thaw studies.

It will also be appreciated that additional antiseptics, disinfectants, or antibiotics may be included and are contemplated. These include, for example, addition of metals such as silver, copper, zinc; iodine and iodophors: "azole" antifungal agents including clortrimazole, miconazole, econazole, ketoconazole, metronizazole, and salts thereof; and the like. Antibiotics such as tobramycin, clindamycin, tetracycline, neomycin sulfate, bacitracin, mupirocin, tetracycline, polymixin, and the like, also may be included. Preferred compositions, however, are free of antibiotics due to the chance of resistance formation.

As indicated above there is also provided herein a method of moisturizing oral tissue of a patient requiring intubation, wherein a cationic antiseptic compatible moisturizer composition is used in conjunction with an endotracheal tube, which is coated or impregnated with the cationic antiseptic. Further, in another embodiment, there is provided a kit comprising a moisturizer composition for application to oral tissue, to an endotracheal tube, or both the oral tissue and the endotracheal tube; and at least one endotracheal tube; wherein the endotracheal tube is coated or impregnated with a cationic antiseptic; wherein the moisturizer composition essentially excludes any component which causes a precipitate when combined with the cationic antiseptic when tested according to Test Method F; and wherein the cationic antiseptic is other than a metal ion. Here the moisturizer composition can be any one of the moisturizer compositions described herein, and can be applied as described herein for any of these compositions. Applying the moisturizer composition can be carried out before, during, or after inserting the endotracheal tube. The moisturizer composition not only provides a moisturizing effect to the patients oral tissue, but can also act as a lubricant to ease insertion of the endotracheal tube. The moisturizer composition can be applied to the patient's oral tissue, to the surfaces of the endotracheal tube, or to both the oral tissue and the endotracheal tube without causing a significant reduction in the antimicrobial activity of the cationic antiseptic associated with the endotracheal tube as a result of contact with between the moisturizer composition and the endotracheal tube.

Endotracheal tubes which can be used in the above method include those described in U.S. Patent Application No. 2009/0032027. Useful endotracheal tube materials includes polyurethane (PU), low-density polyethylene (LDPE), metallocene polyolefins such as metallocene polyethylene and polypropylene, silicones such as silicones cured by moisture or hydrosilation, polyvinyl chloride (PVC), polyamid (PA) or polyesters including elastomeric polyesters such as Hytrel brand polyesters, as well as fluoropolymers such as Teflon and fluoroelastomers as well as blends, mixtures, and laminates or coextrusions thereof, and combinations thereof.

Coated endotracheal tubes can be prepared by applying a cationic antiseptic composition to an endotracheal tube using coating methods such as dip coating, extrusion coating, vapor deposition, spraying, and the like as well as combinations thereof. The cationic antiseptic composition for coating the endotracheal tube includes at least one cationic antiseptic as described herein, an optional suitable carrier for dissolving or dispersing the antiseptic, and optionally a film forming polymer. Suitable cationic antiseptics include the multi-valent cationic antiseptics described above, as well as other cationic antiseptics described in U.S. Patent Application No. 2006/211533, including, for example, small molecule quaternary ammonium compounds such as benzalkoium chloride and alkyl substituted derivatives; di-long chain alkyl (C8-C18) quaternary ammonium compounds; cetylpyridinium halides and their derivatives; benzethonium chloride and its alkyl substituted derivatives; octenidine and combinations thereof.

Preferred carriers do not dissolve or compromise the physical strength and structural integrity of the endotracheal tube. The carrier may attack the substrate temporarily during coating in order to promote adequate bonding of the coating. Suitable carriers include, for example, solvents such as volatile esters, ketones, alkanes, ethers, toluene, xylene as well as water, and combinations thereof.

Optional film forming polymers include polyurethanes, polyvinylchloride, polyacrylates, silicones, fluoropolymers, polyolefins, polyamides, polyethers, copolymers such as ethylene vinylacetate, polymers made from ethylenically unsaturated monomers and combinations thereof. The film forming polymer may be linear, branched, hyperbranched, or crosslinked. See, for example, U.S. Pat. No. 6,949,958.

Endotracheal tubes impregnated with the a multi-valent cationic antiseptic can be prepared by extrusion or curing such as dip coating and subsequently initiating cure.

LISTING OF EMBODIMENTS

The following is a listing of certain of the embodiments described herein:
1. A method of moisturizing while decolonizing mammalian tissue, the method comprising:
    applying a multi-valent cationic antiseptic composition to oral tissue, and
    applying a moisturizer composition to at least a portion of the oral tissue;
    wherein the moisturizer composition essentially excludes any component which causes a precipitate when combined with a multi-valent cationic antiseptic used in the multi-valent cationic antiseptic composition when tested according to Test Method F;
    wherein the multi-valent cationic antiseptic is other than a metal ion.
2. The method of embodiment 1, wherein the essentially excluded component is selected from the group consisting of polyanions of polycarboxylates, polysulfonates, polysulfates, and organic and inorganic polyphosphates; anions of alkylsulfates, arylsulfates, alkylsulfonates, arylsulfonates, alkylcarboxylates, arylcarboxylates, alkylphosphates, arylphosphates; halide salts; and combinations thereof, wherein the alkyl groups have a chain length of greater than 6 carbon atoms and the aryl groups have 6 or more carbon atoms, and wherein the essentially excluded component is not present or present at a concentration less than 0.1 percent by weight of the composition, except halide salts which are not present or present at a concentration not greater than 0.2 wt-% by weight of the composition.
3. The method of embodiment 1 or embodiment 2, wherein the moisturizer composition is such that a log reduction in the number of viable bacterial cells of at least 2 is provided when $10^6$ cfu of *Pseudomonas aeruginosa* (ATCC 27853) are combined with a mixture of 1.1 g of the moisturizer composition and 1.5 g of a multi-valent cationic antiseptic composition containing 0.12 weight percent of the multi-valent cationic antiseptic according to Test Method B.
4. A method of moisturizing while decolonizing mammalian tissue, the method comprising:
    applying a multi-valent cationic antiseptic to the tissue, and
    applying a substantive moisturizer composition to at least a portion of the same tissue;
    wherein the mammalian tissue is oral tissue of a subject;
    wherein the multi-valent cationic antiseptic is other than a metal ion; and
    wherein the substantive moisturizer composition is such that a log reduction in the number of viable bacterial cells of at least 2 is provided when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent of the multi-valent cationic antiseptic according to Test Method B.
5. The method of embodiment 3 or embodiment 4, wherein the moisturizer composition is such that a log reduction in the number of viable bacterial cells of at least 3 is provided.
6. The method of embodiment 4 or embodiment 5, wherein the substantive moisturizer composition essentially excludes a component selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.
7. The method of any one of embodiments 1 through 6, wherein the moisturizer composition has a pH of 3 to 8.
8. The method of any one of embodiments 1 through 7, wherein the moisturizer composition has a viscosity of at least 50 centipoise.
9. The method of any one of embodiments 1 through 8, wherein the multi-valent cationic antiseptic is selected from the group consisting of biguanides, bisbiguanides, polybiguanides, polymeric quaternary ammonium compounds, and combinations thereof.
10. The method of embodiment 9, wherein the multi-valent cationic antiseptic is a chlorhexidine salt.
11. The method of any one of embodiments 1 through 10, wherein the multi-valent cationic antiseptic is included in a composition comprising a solution of the multi-valent cationic antiseptic at 0.05 to 0.4 weight percent.
12. The method of any one of embodiments 1 through 11, wherein the multi-valent cationic antiseptic is included in a composition further comprising a sweetener selected from the group consisting of sucralose, aspartame, xylose, sucrose, maltose, mannose, glucose, xylitol, sorbitol, mannitol, erythritol, maltitol, lactitol, and a combination thereof.
13. The method of any one of embodiments 1 through 12, wherein the substantive moisturizer composition is applied after applying the cationic antiseptic.
14. The method of any one of embodiments 1 through 12, wherein the substantive moisturizer composition is applied before applying the cationic antiseptic.
15. The method of any one of embodiments 1 through 14, wherein the moisturizer composition and the multi-valent cationic antiseptic are applied within 12 hours of each other.
16. The method of any one of embodiments 13, 14, and 15, wherein the substantive moisturizer composition and the multi-valent cationic antiseptic are applied within 4 hours of each other.
17. The method of any one of embodiments 13 through 16, wherein the substantive moisturizer composition and the multi-valent cationic antiseptic are applied within less than 30 minutes of each other.

18. The method of any one of embodiments 1 through 12, wherein the moisturizer composition is applied at the same time as applying the multi-valent cationic antiseptic.
19. The method of any one of embodiments 1 through 18, wherein the moisturizer composition is applied in an amount of 1 to 10 grams per application.
20. The method of any one of embodiments 1 through 19, wherein the moisturizer composition has a shrinkage of less than 10 percent when dried under ambient conditions for 2 hours.
21. The method of any one of embodiments 1 through 20, wherein the substantive moisturizer composition when dried on a surface under ambient conditions cannot be peeled from the surface in a single piece.
22. The method of any one of embodiments 1 through 21, wherein the moisturizer composition when dried on a surface under ambient conditions does not form a self supporting film.
23. The method of any one of embodiments 1 through 22, further comprising applying a de-briding composition comprising hydrogen peroxide.
24. The method of embodiment 23, wherein the hydrogen peroxide is stabilized with a component which maintains the de-briding composition at a pH of 2.5 to 4, and wherein the de-briding composition essentially excludes any component which causes a precipitate when combined with a multi-valent cationic antiseptic used in the multi-valent cationic antiseptic composition when tested according to Test Method F.
25. The method of embodiment 24, wherein the hydrogen peroxide is stabilized with a buffer component selected from the group consisting of monovalent alkyl carboxylic acids and alkyl phosphoric acids wherein the alkyl group optionally comprises a carbon chain substituted with or interrupted by one or more N, O, or S atoms; phosphate or carboxylate terminated polyethoxylated and/or propoxylated alkyl alcohols; alpha-hydroxy acids; amino acids; phosphoric acid; and boric acid; wherein the buffer component is selected and used at concentrations such that a precipitate is not formed when the buffer component is combined with the multi-valent cationic antiseptic.
26. The method of any one of embodiments 1 through 25, wherein the oral tissue is oral mucosal tissue.
27. The method of embodiment 26, wherein the oral mucosal tissue is selected from the group consisting gingiva, buccal mucosa, the floor of the mouth, the hard palate, the soft palate, the dorsal tongue, the lateral tongue, the ventral tongue, an oropharyngeal surface, and combinations thereof.
28. The method of any one of embodiments 1 through 27, wherein the subject is a patient in an Intensive Care Unit.
29. The method of any one of embodiments 1 through 28, wherein the subject is a mechanically ventilated patient.
30. An oral care kit comprising:
a multi-valent cationic antiseptic composition comprising a multi-valent cationic antiseptic; and
a moisturizer composition;
wherein each composition is for application to oral tissue of a subject;
wherein the moisturizer composition essentially excludes any component which causes a precipitate when combined with the multi-valent cationic antiseptic when tested according to Test Method F;
wherein the multi-valent cationic antiseptic is other than a metal ion.
31. The oral care kit of embodiment 30, wherein the essentially excluded component is selected from the group consisting of polyanions of polycarboxylates, polysulfonates, polysulfates, and organic and inorganic polyphosphates; anions of alkylsulfates, arylsulfates, alkylsulfonates, arylsulfonates, alkylcarboxylates, arylcarboxylates, alkylphosphates, arylphosphates; halide salts; and combinations thereof, wherein the alkyl groups have a chain length of greater than 6 carbon atoms and the aryl groups have 6 or more carbon atoms, and wherein the essentially excluded component is not present or present at a concentration less than 0.1 percent by weight of the composition, except halide salts which are not present or present at a concentration not greater than 0.2 wt-% by weight of the composition.
32. The oral care kit of embodiment 30 or embodiment 31, wherein the moisturizer composition is such that a log reduction in the number of viable bacterial cells of at least 2 is provided when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent of the multi-valent cationic antiseptic according to Test Method B.
33. An oral care kit comprising:
a multi-valent cationic antiseptic composition comprising a multi-valent cationic antiseptic; and
a substantive moisturizing composition;
wherein each composition is for application to oral tissue of a subject;
wherein the multi-valent cationic antiseptic is other than a metal ion; and
wherein the substantive moisturizer composition is such that a log reduction in the number of viable bacterial cells of at least 2 is provided when $10^6$ cfu of *Pseudomonas aeruginosa* (ATCC 27853) are combined with a mixture of 1.1 g of the substantive moisturizer composition and 1.5 g of the multi-valent cationic antiseptic composition containing 0.12 weight percent of the multi-valent cationic antiseptic according to Test Method B.
34. The oral care kit of embodiment 33, wherein the substantive moisturizer composition is such that a log reduction in the number of viable bacterial cells of at least 3 is provided.
35. The oral care kit of embodiment 33 of embodiment 34, wherein the substantive moisturizer composition essentially excludes a component selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.
36. The oral care kit of any one of embodiments 30 through 35, wherein the moisturizer composition has a pH of 3 to 8.
37. The oral care kit of any one of embodiments 30 through 36, wherein the moisturizer composition has a viscosity of at least 50 centipoise.
38. The oral care kit of any one of embodiments 30 through 37, wherein the multi-valent cationic antiseptic is selected from the group consisting of biguanides, bisbiguanides, polybiguanides, polymeric quaternary ammonium compounds, and combinations thereof.
39. The oral care kit of embodiment 38, wherein the multi-valent cationic antiseptic is a chlorhexidine salt.
40. The oral care kit of any one of embodiments 30 through 39, wherein the multi-valent cationic antiseptic composition comprises a solution of the multi-valent cationic antiseptic at 0.05 to 0.4 weight percent.

41. The oral care kit of any one of embodiments 30 through 40, wherein the multi-valent cationic antiseptic is included in a composition further comprising a sweetener selected from the group consisting of sucralose, aspartame, xylose, sucrose, maltose, mannose, glucose, xylitol, sorbitol, mannitol, erythritol, maltitol, lactitol, and a combination thereof.

42. The oral care kit of any one of embodiments 30 through 41, wherein the kit includes at least one dose of the multi-valent cationic antiseptic composition.

43. The oral care kit of any one of embodiments 30 through 42, wherein the kit includes at least 15 mL of the multi-valent cationic antiseptic composition.

44. The oral care kit of any one of embodiments 30 through 43, wherein the kit includes at least 30 mL of the multi-valent cationic antiseptic composition.

45. The oral care kit of any one of embodiments 30 through 44, wherein the kit includes at least two 15 mL unit dose containers of the multi-valent cationic antiseptic composition.

46. The oral care kit of any one of embodiments 30 through 45, wherein the moisturizing composition is supplied in an amount sufficient for at least one application to the oral tissue of the subject at 1 to 10 grams per application.

47. The oral care kit of any one of embodiments 30 through 46, wherein the substantive moisturizing composition is supplied in an amount sufficient for at least 4 applications to the oral tissue of the subject at 1 to 10 grams per application.

48. The oral care kit of embodiment 47, wherein the moisturizing composition is supplied in at least 4 unit dose packages of 1 to 10 grams per package.

49. The oral care kit of any one of embodiments 30 through 48, wherein the moisturizing composition is supplied in a single container.

50. The oral care kit of any one of embodiments 30 through 49, wherein the moisturizer composition has a shrinkage of less than 10 percent when dried under ambient conditions.

51. The oral care kit of any one of embodiments 30 through 50, wherein the substantive moisturizer composition when dried on a surface under ambient conditions cannot be peeled from the surface in a single piece.

52. The oral care kit of any one of embodiments 30 through 51, wherein the moisturizer composition when dried on a surface under ambient conditions does not form a self supporting film.

53. The oral care kit of any one of embodiments 30 through 52, wherein the kit further comprises a de-briding composition.

54. The oral care kit of embodiment 53, wherein the de-briding composition comprises hydrogen peroxide stabilized with a component which maintains the de-briding composition at a pH of 2.5 to 4, and wherein the de-briding composition essentially excludes any component which causes a precipitate when combined with a multi-valent cationic antiseptic used in the multi-valent cationic antiseptic composition when tested according to Test Method F.

55. The oral care kit of embodiment 54, wherein the hydrogen peroxide is stabilized with a buffer component selected from the group consisting of monovalent alkyl carboxylic acids and alkyl phosphoric acids wherein the alkyl group optionally comprises a carbon chain substituted with or interrupted by one or more N, 0, or S atoms; phosphate or carboxylate terminated polyethoxylated and/or propoxylated alkyl alcohols; alpha-hydroxy acids; amino acids; phosphoric acid; and boric acid; wherein the buffer component is selected and used at concentrations such that a precipitate is not formed when the buffer component is combined with the multi-valent cationic antiseptic.

56. The oral care kit of any one of embodiments 53, 54, and 55, wherein the de-briding composition is supplied in an amount sufficient for at least one application to the oral tissue of the subject.

57. The oral care kit of embodiment 56, wherein the de-briding composition is supplied in at least 4 unit dose containers, each containing an amount sufficient for a single application to the oral tissue of the subject.

58. The oral care kit of embodiment 57, wherein the de-briding composition is supplied in a single container in an amount sufficient for at least 4 applications to the oral tissue of the subject.

59. The oral care kit of any one of embodiments 30 through 58, further comprising an additional oral care composition selected from the group consisting of an oral rinse, a toothpaste, a lip care composition, a mouth care composition, and combinations thereof.

60. The oral care kit of any one of embodiments 30 through 59, further comprising a plurality of applicator tools for applying at least one composition to the oral tissue of a subject.

61. The oral care kit of embodiment 60, wherein the plurality of applicator tools is selected from the group consisting of swabs, suction swabs, toothbrushes, suction toothbrushes, and combinations thereof.

62. The oral care kit of embodiment 60 or embodiment 61, wherein at least a portion of the plurality of applicator tools is packaged so that usage of the at least a portion of the plurality of applicator tools shows compliance with at least a portion of a protocol for treating the oral tissue of a subject.

63. The oral care kit of embodiment 62, wherein the at least a portion of the plurality of applicator tools is packaged with an indication of at least one time frame for applying at least one composition comprising the kit.

64. The oral care kit of embodiment 63, wherein the indication is a color code, a symbol, a picture, or a printed number.

65. The oral care kit of any one of embodiments 60 through 64, comprising a plurality of packages, wherein each package contains at least one kit component selected from the group consisting of an applicator tool, a suction yankaeur, a suction catheter, a Y-connector, a vacuum adapter handle, a multi-valent cationic antiseptic composition, a substantive moisturizing composition, a de-briding composition, other mouth care products and a combination thereof.

66. The oral care kit of embodiment 65, wherein the package is a bag, a box, a tray, or a combination thereof.

67. A method of moisturizing while decolonizing mammalian tissue, the method comprising:
applying a multi-valent cationic antiseptic composition to the tissue, and
applying a substantive moisturizer composition to at least a portion of the same tissue;
wherein the mammalian tissue is oral tissue of a subject;
wherein the multi-valent cationic antiseptic is other than a metal ion; and
wherein when the substantive moisturizer composition includes an anionic compound, the anionic compound is such that the multi-valent cationic antiseptic composition combined with the substantive moisturizer composition achieves a log reduction in the number of viable bacterial cells of at least 2 when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent of the multi-valent cationic antiseptic according to Test Method B; and wherein the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

68. A method of moisturizing while decolonizing mammalian tissue, the method comprising:

applying a multi-valent cationic antiseptic composition to the tissue, and applying a substantive moisturizer composition to at least a portion of the same tissue;

wherein the mammalian tissue is oral tissue of a subject;

wherein the multi-valent cationic antiseptic is other than a metal ion; and wherein when the substantive moisturizer composition includes an anionic compound, the anionic compound is such that greater than 40 percent of the multivalent cationic antiseptic, which was soluble in the multi-valent cationic antiseptic composition, remains soluble when the multi-valent cationic antiseptic composition and the substantive moisturizer composition are combined; and wherein the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

69. An oral care kit comprising:

a multi-valent cationic antiseptic composition comprising a multi-valent cationic antiseptic; and a substantive moisturizing composition;

wherein each composition is for application to oral tissue of a subject;

wherein the multi-valent cationic antiseptic is other than a metal ion; and wherein when the substantive moisturizer composition includes an anionic compound, the anionic compound is such that the multi-valent cationic antiseptic composition combined with the substantive moisturizer composition achieves a log reduction in the number of viable bacterial cells of at least 2 when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent of the multi-valent cationic antiseptic according to Test Method B; and wherein the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

70. An oral care kit comprising:

a multi-valent cationic antiseptic composition comprising a multi-valent cationic antiseptic; and a substantive moisturizing composition;

wherein each composition is for application to oral tissue of a subject;

wherein the multi-valent cationic antiseptic is other than a metal ion; and wherein when the substantive moisturizer composition includes an anionic compound, the anionic compound is such that greater than 40 percent of the multivalent cationic antiseptic which was soluble in the multi-valent cationic antiseptic composition remains soluble when the multi-valent cationic antiseptic composition and the substantive moisturizer composition are combined; and wherein the anionic compound is selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

71. The method of embodiment 67 or embodiment 68 or the oral care kit of embodiment 69 or embodiment 70, where the substantive moisturizer composition when dry does not form a self supporting film.

72. A method of moisturizing oral tissue of a patient requiring intubation, the method comprising:

applying a moisturizer composition to at least a portion of the oral tissue, an endotracheal tube, or both;

inserting an endotracheal tube through the patients oral cavity and into the patient's trachea;

wherein the endotracheal tube is coated or impregnated with a cationic antiseptic;

wherein the moisturizer composition essentially excludes any component which causes a precipitate when combined with the cationic antiseptic when tested according to Test Method F; and wherein the cationic antiseptic is other than a metal ion.

73. A kit comprising:

a moisturizer composition for application to oral tissue, to an endotracheal tube, or both; and at least one endotracheal tube;

wherein the endotracheal tube is coated or impregnated with a cationic antiseptic;

wherein the moisturizer composition essentially excludes any component which causes a precipitate when combined with the cationic antiseptic when tested according to Test Method F; and wherein the cationic antiseptic is other than a metal ion.

Objects and advantages of this invention are further illustrated by the following examples, but the particular materials and amounts thereof recited in these examples, as well as other conditions and details, should not be construed to unduly limit this invention.

EXAMPLES

TABLE 1

| \multicolumn{5}{c}{GLOSSARY of COMPONENTS} |

| Acronym | Description | Trade Name | Source | Location |
|---|---|---|---|---|
| — | *Aloe Vera* Gel | *Aloe Vera* Gel Concentrate | Concentrated *Aloe* Corporation | Ormond Beach, FL |
| — | *Aloe Vera* Gel | *Aloe barbadensis* leaf juice, 1x, decolorized) | Terry Laboratories | Chicago, IL |
| — | Benzoic Sulphimide Sodium Salt - 97% | Sodium Saccharin | Alfa Aesar, lot # IN000161 | Pelham, NH |
| — | Carbomer 954 | Carbopol 954 | BFGoodrich, lot# 6900029 | Cleveland, OH |
| — | L-carvone | — | Ungerer & Co | Lincoln Park, NJ |
| CHG | Chlorhexidine Digluconate | Chlorhexidine Gluconate 20% USP (18.6% wt/wt) | American International Chemical Inc. | Framingham, MA |
| — | Citric Acid-Anhydrous | — | Sigma, lot # 023K0023 | St. Louis, MO |
| — | D-Gluconic Acid | | Aldrich | St. Louis, MO |
| — | Glycerol | Glycerin USP | J.T. Baker | Phillipsburg, NJ |
| — | Glycerol | Glycerin USP | Ecogreen | Cranbury, NJ |
| — | Glyceryl Polymethacrylate | — | international Specialty Products (ISP) | Wayne, NJ |
| HEC | (hydroxyethylcellulose) | Natrosol 250H | Hercules | Shandong China |
| — | Hydroxypropyl Guar | Jaguar HP 60 | Rhodia | Cranbury, NJ |
| HPMC | Hydroxypropylmethyl-cellulose | Methocel K100M Premium | Dow Chemical Company | Midland, MI |
| — | Menthol USP | — | Sharp Menthol India Ltd | Delhi, India |
| — | Methylparaben | — | Sharon Laboratories | Israel |
| — | Peppermint - Natural | — | Intarome | Norwood, NJ |
| $H_3PO_4$ | Phosphoric Acid - 85% | — | Aldrich Chemical Co., lot# 11430KY | Milwaukee, WI |
| KCl | Potassium Chloride | — | J.T. Baker, lot# G28H00 | Phillipsburg, NJ |
| — | Potassium Sorbate | — | J.T. Baker, lot# E27620 | Phillipsburg, NJ |
| — | Propylparaben | — | Sharon Laboratories | Israel |
| $C_6H_5COONa$ | Sodium Benzoate | — | Alfa Aesar, lot# 10102000 | Pelham, NH |
| NaCMC | Sodium Carboxymethyl cellulose | — | Fisher Scientific Co., lot# 794429 | Fairlawn, NJ |
| NaCl | Sodium Chloride | Table salt | Sigma-Aldrich | St. Louis, MO |
| NaCl | Sodium Chloride | Table salt | J.T. Baker, lot# G32468 | Phillipsburg, NJ |
| NaOH | Sodium Hydroxide | — | Titristar, lot# 3120 | Gibbstown, NJ |
| — | Spearmint - Imitation | — | Belwood Aromatics | Ringwood, NJ |
| $H_2O$ | Water - Purified Distilled Water | — | 3M Laboratory | St. Paul, MN |
| — | Xanthan Gum | Keltrol TF | CP Kelco | San Diego, CA |
| — | Xylitol | Xylitol NF/FCC | American International Chemical Inc. | Framingham, MA |
| — | Xylitol | Xylitol NF/FCC | Futian Pharmaceutical | Melbourne, FL |

TABLE 2

Comparative Examples of Commercially Available Oral Moisturizers

| Comparative Example Number | Product Name | Manf. | Ingredients (in order of predominance as appearing on product label) |
|---|---|---|---|
| C1 | Biotene ORALBALANCE gel | Laclede Inc. | Hydrogenated starch hydrolysate, Glycerin polymethacrylate, Xylitol, Hydroxyethyl cellulose, Beta-d-glucose, Lactoperoxidase, Lysozyme, Lactoferrin, Glucose oxidase, Potassium thiocyanate, *Aloe Vera* |
| C2 | KIMVENT Mouth Moisturizer | Kimberly-Clark | Purified Water, Propylene Glycol, Sorbitol, Hydroxypropyl Methylcellulose, Dimethicone, Flavor, Xylitol, *Aloe Vera* Gel, Potassium Sorbate, Sodium Benzoate, Potassium Chloride, Sodium Chloride |
| C3 | TOOTHETTE Mouth Moisturizer | Sage Products Inc. | Water, Coconut Oil, Xylitol, Spearmint flavor, Sodium Carboxymethylcellulose, Vitamin E Acetate, Spearmint oil, Carbomer 974, Polysorbate 20, polysorbate 80, potassium sorbate, cetylpyridinium chloride |
| C4 | Biotene Mouthwash | Laclede Inc. | Purified Water, Propylene Glycol, Xylitol, Polyglycitol, Poloxamer 407, Hydroxyethylcellulose, Sodium Benzoate, Benzoic Acid, Natural Peppermint, Sodium Phosphate, Zinc Gluconate, Calcium Lactate, *Aloe Vera*, Potassium Thiocyanate, Natural Enzymes: Lactoferrin, Lysozyme, Lactoperoxidase, Glucose Oxidase |

TABLE 3

Example Formulations of Moisturizers

| Example Number | Example Name | Ingredients (% w/w) |
|---|---|---|
| Ex 1 | Example 1 | Purified Water (87.8%), Xylitol (5%), Glycerol (5%), Xanthan Gum (1.6%), Hydroxypropylmethylcellulose (0.5%), *Aloe Vera* Gel (0.1%) |
| Ex 2 | Example 2 | Purified Water (87.8%), Xylitol (5%), Glycerol (5%), Hydroxypropyl Guar (1.6%), Hydroxypropylmethylcellulose (0.5%), *Aloe Vera* Gel (0.1%) |
| Ex 3 | Example 3 | Purified Water (87.8%), Xylitol (5%), Glycerol (5%), Hydroxypropyl Guar (1.6%), Hydroxypropylmethylcellulose (0.5%), Chlorhexidine Digluconate (0.12%), *Aloe Vera* Gel (0.1%) |
| Ex 4 | Example 4 | Purified Water (80.71%), Glycerin (15%), Hydroxypropyl Guar (1%), Hydroxyethylcellulose (1%), Xylitol (1%), *Aloe Vera* Gel (1%), Methylparaben (0.2%), Propylparaben (0.04%), Imitation Spearmint (0.0225%), Menthol (0.015%), Natural Peppermint (0.01%), L-carvone (0.0025%) |

Test Method A—Viscosity Test

For selected Examples viscosity was measured at approximately 22° C. at ambient pressure using a Brookfield viscometer, model LVT with Brookfield LV spindles. The smallest spindle and the lowest speed are always chosen for each particular sample such that the viscometer was operating in the middle of its range. All samples were allowed to equilibrate at approximately 22° C. for 24 hours prior to measurement. Preferably the viscosity is taken at the lowest speed possible while staying within 10-90% and preferably 20-80% of the viscometer range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The viscosity of each sample was taken as the highest relatively stable reading that was achieved.

TABLE 4

Viscosity Results

| Example Number | Product Name | Viscosity (cps) |
|---|---|---|
| C1 | ORALBALANCE Gel | >2,000,000 |
| C2 | KIMVENT Mouth Moisturizer | 80,000 |

TABLE 4-continued

Viscosity Results

| Example Number | Product Name | Viscosity (cps) |
|---|---|---|
| C3 | TOOTHETTE Mouth Moisturizer | 1,810,000 |
| C4 | Biotene Mouthwash | 18 |
| Ex 1 | Example 1 | 80,000 |
| Ex 2 | Example 2 | 290,000 |
| Ex 3 | Example 3 | Not tested |
| Ex 4 | Example 4 | 77,000 |

Test Method B—Antimicrobial Efficacy Testing

This test method demonstrates the compatibility (or incompatibility) of PERIDEX antimicrobial mouth rinse with mouth moisturizers by challenging the mixtures with the bacteria *Pseudomonas aeruginosa*. If the activity of PERIDEX mixed with a moisturizer is not statistically less than the activity of PERIDEX alone, then the moisturizer can be said to be compatible with PERIDEX. The ratio of PERIDEX:Moisturizer was chosen to mimic actual product use. When PERIDEX is applied using a swab to a ventilated patient approximately 1 to 2 grams is retained in the oral cavity. Many moisturizers are supplied in 2 g unit does packets, from which approximately 1 to 2 grams can be applied. In this assay, the antimicrobial activity of mixtures of PERIDEX and moisturizers is tested by inoculating 1 mL of the mixture with an inoculum of the bacteria. At the specified exposure time, a neutralizer for CHG and hydrogen peroxide is added, tubes are vortexed, serially diluted and plated for enumeration of surviving bacteria.

Sample Preparation for Antimicrobial Efficacy Test

Test mixtures were prepared at 2 levels (4.8 g or 6.4 g) of each of the above moisturizers with 9 g of PERIDEX solution. PERIDEX is a solution of 0.12% chlorhexidine gluconate (1,11-hexamethylene bis[5-(p-chlorophenyl)biguanide]di-D-gluconate) in a base containing water, 11.6% alcohol, glycerin, PEG-40 sorbitan diisostearate, flavor, sodium saccharin, and FD&C Blue No. 1 commercially available from 3M ESPE Dental Products of St. Paul, Minn. The resulting mixtures were vortexed to mix vigorously for a period of 2 minutes. The mixtures were allowed to incubate for 15 minutes prior to centrifugation at 5000 rpm for 30 min. The samples were centrifuged in order to settle insoluble material. After centrifugation, supernatant was carefully transferred to a new vial and submitted for Antimicrobial Efficacy Testing, see Table 5 and HPLC recovery of CHG testing, see Table 7.

Test Organism for Antimicrobial Efficacy Test

The test organism for this assay was *Pseudomonas aeruginosa* (ATCC 27853). The initial suspension was prepared by suspending bacterial colonies from an overnight growth plate on Tryptic Soy Agar in phosphate-buffered water (PBW). The PBW was prepared as follows: To 500 ml deionized water was added 0.34 g potassium dihydrogen phosphate. The pH was adjusted to 7.2 using 10N sodium hydroxide. The contents were diluted to 1 liter using deionized water. This was filter sterilized. A 0.5 McFarland turbidity standard was used to obtain a cell density of approximately $1.5 \times 10^8$ CFU/mL.

Test Materials for Antimicrobial Efficacy Test

Each moisturizer was mixed with PERIDEX in defined ratios as described above. PERIDEX and moisturizer were weighed into glass vials, and mixed by vortexing for a period of 2 minutes. Moisturizer samples containing CHG were not mixed with PERIDEX. Testing was conducted with 1 mL of the mixtures. Duplicate 1 mL samples were transferred into 50 mL conical tubes with a positive displacement pipet. The controls for the testing were 1 mL of PBW (for direct enumeration of inoculum) and 1 mL PERIDEX.

Inoculum Preparation for Antimicrobial Efficacy Test

The inoculum was prepared by diluting the initial suspension 10 fold in PBW. The inoculum suspension was enumerated at the beginning and end of the test period. The final count was within 0.1 log/mL of the initial count. Each 1 mL test sample was inoculated with approximately 5.8 logs bacteria.

Neutralizing Broth: The D/E broth is Dey Engley neutralizing broth purchased as a solid and reconstituted according to directions from Difco Laboratories, Detroit Mich. The D/E broth was supplemented with filter-sterilized Catalase (from bovine liver, Calbiochem, 0.2 g/liter broth) immediately before use.

Test Method B—Measurement of Antimicrobial Activity:

Forty microliters of the bacterial inoculum was added to one mL of the test mixtures, vortexed and let sit at ambient temperature. Timing started as soon as the bacteria were added. After 2.5 minutes, 20 mL of D/E broth containing catalase was added and vortexed vigorously.

Dilutions were prepared in PBW, and 1 mL, in duplicate, pipetted into Aerobic Count Petrifilm Plates, 3M Company. All plates were incubated at 35° C. for 43 hours. Plates were counted with the 3M Petrifilm Plate Reader, and confirmed manually. Colony Forming Units (CFU) were counted, duplicate plates averaged and multiplied by the dilution factor for CFU/mL, and multiplied by the total test volume after neutralization (21 mL) for the CFU/test sample. Log 10 CFU/test of duplicate tests were averaged and the log 10 reduction was calculated from the PBW controls.

The mixtures of PERIDEX with the comparative examples C1, C2, C3 and experimental examples Ex 1, Ex 2 and Ex 3 were tested according to the above Antimicrobial Efficacy Test. The results are shown in Table 5, below. Mixtures of PERIDEX with KIMVENT Mouth Moisturizer, 3M Xanthan Gel and 3M Guar Gel did not significantly impact the antimicrobial efficacy of CHG. All performed equivalent to PERIDEX oral rinse tested under the same conditions. 3M Guar Gel with 0.12% CHG also performed similarly to the PERIDEX control. In contrast, mixtures of PERIDEX with ORALBALANCE Gel and TOOTHETTE Mouth moisturizer significantly decreased the antimicrobial efficacy of CHG. Both ORALBALANCE Gel and TOOTHETTE moisturizers achieved less than 2 log reduction of bacteria.

TABLE 5

RESULTS FOR TEST METHOD B - ANTIMICROBIAL EFFICACY TEST

| Moisturizer Example Number | Grams of PERIDEX | Grams of Moisturizer | Log Reduction |
|---|---|---|---|
| C1 | 1.5 | 0.8 | 1.5 |
| C1 | 1.5 | 1.1 | 1.5 |
| C3 | 1.5 | 0.8 | 0.5 |
| C3 | 1.5 | 1.1 | 0.6 |
| Ex 1 | 1.5 | 0.8 | 4.6 |
| Ex 1 | 1.5 | 1.1 | 5.0 |
| Ex 2 | 1.5 | 0.8 | 5.4 |
| Ex 2 | 1.5 | 1.1 | 5.7 |
| Ex 3 | 0 | 1.1 | 4.3 |
| Control* | 1.5 | 0 | 5.7 |

*Control = PERIDEX only

The TOOTHETTE mouth moisturizer C3 was tested in increasing ratios of moisturizer:PERIDEX according to the Antimicrobial Efficacy Test, described above. The results are shown in Table 6, below. Virtually complete kill of bacteria is achieved with PERIDEX when it is uninhibited by moisturizer C3. However, as little as 0.2 grams of TOOTHETTE moisturizer impacts the antimicrobial efficacy of PERIDEX. With increasing levels of moisturizer C3, the log reduction is further reduced.

Additional test mixtures were prepared across a range of levels (1.2 g, 2.4 g, 4.8 g, 6.0 g, and 6.4 g) of commercially available C3 moisturizer (TOOTHETTE Mouth Moisturizer), each weighed into a vial containing 9 g of PERIDEX solution. The resulting mixtures were vortexed for a period of 2 minutes. The mixtures were allowed to incubate for 15 minutes prior to centrifugation at 5000 rpm for 30 min. After centrifugation, supernatant was carefully transferred to a new vial and submitted for Antimicrobial Efficacy Testing, see Table 6 and HPLC recovery of CHG testing, see Table 8.

TABLE 6

ANTIMICROBIAL EFFICACY TEST RESULTS
Increasing Amounts of C3 Moisturizer

| Grams of C3 Moisturizer | Grams of PERIDEX | Average Log Reduction |
|---|---|---|
| 0.2 | 1.5 | 1.9 |
| 0.4 | 1.5 | 1.3 |
| 0.8 | 1.5 | 0.5 |
| 1.0 | 1.5 | 0.6 |
| 1.1 | 1.5 | 0.6 |
| Control 0.0 | 1.5 | 5.7 |

Test Method C—Percent Recovery of CHG by HPLC Analysis

HPLC analysis was performed to approximate the amount of available CHG, not "inhibited" by the moisturizer. Reverse phase gradient HPLC analysis of the provided solutions/suspensions were performed using an Agilent 1200 SLMSD system consisting of a binary SL pump, well plate autosampler, heated column compartment and diode array absorbance detector (DAD). Separations were performed under the following chromatographic conditions. The sample injection volume was 10 µL. The HPLC column used was a 4.6×75 mm, Zorbax 3.5 µm SB-C18 column (Agilent). Column temperature was maintained at 35° C. The flow rate was 0.5 mL/min. The mobile phase consisted of 2 solvent mixtures: solvent A=100% water+0.1% v/v TFA and Solvent B=100% Methanol+0.1% v/v TFA. A programmed linear gradient mobile phase was used: 90/10 Solvent A/Solvent B (0 minute hold) to 100% B (5 minute hold) over eight minutes (linear). Step back to initial conditions, 5 minute re-equilibration. Elution time for chlorhexidine was approximately 13.1 minutes. Detection was by UV-VIS at 258 nm (reference=450 nm). A linear regression calibration curve of the equivalent chlorhexidine response was performed using volumetric standard solutions at 4 levels of chlorhexidine free base. The standards were run both before and after the sample injections. Absorbance data was averaged from duplicate injections from each sample, as well as duplicate samples and concentrations determined based on standards. The equivalent concentrations of CHG were calculated based on the 1.78 fold difference in molecular weights. The CHG control-PERIDEX control is calculated to be 0.133 wt % from HPLC.

Prior to analysis by HPLC samples were prepared in the following manner. Quantitatively, 50-150 mg of each of the above test mixtures were transferred to a vial. An amount of 5 mL of extraction solvent (90/10 water/methanol+0.1% v/v TFA) was added to the test mixtures. All samples were vortexed briefly and allowed to extract/dissolve for a period of 4 hours at room temperature on an orbital shaker. After extraction for 4 hours, samples were transferred to HPLC vials. Samples were ready for HPLC analyses.

TABLE 7

HPLC % Recovery of CHG in the Presence of Different Types of Moisturizers

| Moisturizer | Grams of PERIDEX | Grams of Moisturizer | % Recovery of CHG |
|---|---|---|---|
| C1 (ORALBALANCE) | 1.5 | 1.1 | 33.3% |
| C2 (KIMVENT) | 1.5 | 1.1 | 104.4% |
| C3 (TOOTHETTE) | 1.5 | 1.1 | 26.7% |
| Ex 1 (Xanthan gel) | 1.5 | 1.1 | 97.8% |
| Ex 2 (Guar gel) | 1.5 | 1.1 | 106.7% |
| Ex 3 (Guar gel + CHG) | 1.5 | 1.1 | 100.0% |
| Control (PERIDEX only) | 1.5 | 0 | 100.0% |

Percent Recovery of soluble CHG was compared to control using 90% water/10% methanol/0.1% TFA for solubilization of CHG

TABLE 8

HPLC % Recovery of CHG in the Presence of Different Levels of Moisturizer

| Grams of C3 Moisturizer | Grams of PERIDEX | % Recovery of CHG |
|---|---|---|
| 0.2 | 1.5 | 40.3% |
| 0.4 | 1.5 | 25.0% |
| 0.8 | 1.5 | 18.2% |
| 1.0 | 1.5 | 13.2% |
| Control 0.0 | 1.5 | 100.0% |

% Recovery of soluble CHG was compared to control using 90% water/10% methanol/0.1% TFA for solubilization of CHG Still more test mixtures were prepared with different amounts of potentially inhibitory reagents including: Carbopol and NaCl, each weighed into a vial containing an equal amount of PERIDEX solution, resulting in 1:1 mixtures as shown in Table 9. The resulting mixtures were vortexed for a period of 2 minutes. The mixtures were allowed to stand at ambient conditions for 15 minutes prior to centrifugation at 5000 rpm for 30 min. After centrifugation, supernatant was carefully transferred to a new vial and submitted for Test Method C, HPLC recovery of CHG testing, see Table 9.

TABLE 9

HPLC % Recovery of CHG in the Presence of Inhibitory Reagents

| Description of Samples | % Recovery of CHG |
|---|---|
| 1:1 soln of 1% Carbopol 954:PERIDEX | 17.91% |
| 1:1 soln of 10% Carbopol 954:PERIDEX | 17.91% |
| 1:1 soln of 1% NaCl:PERIDEX | 38.91% |
| 1:1 soln of 10% NaCl:PERIDEX | 28.36% |
| Control (PERIDEX only) | 100.00% |

% Recovery of soluble CHG was compared to control using 90% water/10% methanol/0.1% TFA for solubilization of CHG Test Method D—Moisturizer Film Formation and Caking An amount of 0.2 grams of a moisturizer was weighed onto the center of a 2.5×2.5 cm (1×1 inch) square marked on a clear plastic petri dish, 15 mm polystyrene plastic disposable sterile dish (Cat #25384-088, VWR West Chester, Pa.). The 0.2 grams of moisturizer was spread evenly to completely coat the 2.5×2.5 cm (1×1 inch) area of a clear plastic petri dish. Films were left to dry at room temperature in open air conditions for 2 hours. After 2 hours, visual and physical observations were made for each dried film. The fraction of area still covered by the dried film was visually observed. Films were physically characterized by peeling the film off of the plastic dish and observing the amount peeled off of the petri dish as a single piece, and the ease with which the film can be torn or broken when pulled. Results are shown in Table 10, below.

TABLE 10

Moisturizer Film Formation Results

| Moisturizer | Film Contraction | Film Peeling |
|---|---|---|
| C2 | The film shrank significantly. Only ⅓ of the 2.5 cm square area was covered | The entire film was removed as a single piece. It was a self-supporting film. The piece was elastic and could not be easily broken or torn. |
| Ex 1 | The entire 2.5 cm square area remained coated | No significant portion of the film was able to be peeled off of the petri dish. A self-supporting film could not be recovered. |
| Ex 2 | The entire 2.5 cm square area remained coated | Approximately ¼ of the coated area was peeled off as a single piece before breaking. The film was very thin, non-elastic and easily torn. The portion that could be removed formed a self-supporting film. |

Test Method E—Demonstration of Substantivity
General Description of Substantivity Test Method:

A substantive moisturizer composition was defined by the ease with which dyed moisturizer sample was washed away from an artificial skin surface, VITRO-SKIN available from IMS Inc. of Portland, Md.). Moisturizer samples included competitive sample C4, Example Ex4, dilutions of Ex4 in distilled water (represented as wt % Ex4), and distilled water alone as a control.

Viscosity Measurement of Moisturizer Samples:

The viscosity of each moisturizer sample or diluted moisturizer sample was measured using a Brookfield viscometer; model LVT with Brookfield LV spindles, as described in the viscosity test. The viscosity of each sample is shown with the results in Table 11.

Dying of Moisturizer Samples for Substantivity Testing:

After measurement of viscosity, each sample was dyed to make the moisturizer sample easily visible in water. The dye was selected to ensure that it does not stain VITRO-SKIN. For the current example, moisturizers were dyed by adding 0.3 grams of BETADINE (10% Povidone Iodine, available from Purdue Products L.P. of Stamford, Conn.) to 5 grams of moisturizer or diluted moisturizer sample. The staining of VITRO-SKIN was verified by placing a drop of BETADINE on the topography side of VITRO-SKIN (prepared as described below), waiting for 1 minute, washing it off in distilled water, and visually confirming the absence of color. For moisturizer samples that are incompatible with povidone iodine, another dye could be used that, similarly, does not stain VITRO-SKIN.

Preparation of VITRO-SKIN for Substantivity Testing:

VITRO-SKIN was pre-hydrated in a chamber at 75° F. (24° C.) and 45% relative humidity (RH). The pre-hydrated VITRO-SKIN was cut into 2.5×2.5 cm (1×1 inch) squares and a black permanent ink marker was used to mark the edges of VITRO-SKIN to make it more visible for manipulation. The squares of VITRO-SKIN were dunked in distilled water for 5 seconds to simulate a moist tissue surface, and placed at the bottom of a dry 8 oz. glass jar, with the topography (non-shiny) side facing up.

Substantivity Test Method:

Each dyed sample (0.5 grams) was pipetted onto the surface of the prepared VITRO-SKIN square in the bottom of its 8 oz. glass jar. Observations were made regarding the surface interaction between the sample and the VITRO-SKIN. Distilled water (25 mL) was added to the jar by pipetting the water down the side of the jar, carefully, to ensure that the contact between the sample and the VITRO-SKIN was not disturbed by the flow of water. After 1 minute (starting at the time water begins to enter the jar), the VITRO-SKIN and any contacting, dyed sample was carefully removed from the jar using tweezers, placed on a clean, dry paper towel, and photographed. The sample was carefully returned to the jar and re-submerged in the water, where it was allowed sit for approximately 1 hour and 30 minutes. After 1 hour and 30 minutes, the VITRO-SKIN and any contacting, dyed sample was, again, carefully removed from the jar using tweezers, placed on a clean, dry paper towel, and photographed. The photographed images were visually characterized according to the amount of surface area covered by the dyed sample, the intensity of the dyed sample, and the relative thickness of the film or pool of dyed sample remaining on the VITRO-SKIN. The results for substantivity of the tested moisturizers are summarized in Table 11 with reported observations made initially, after 1 minute and after 1.5 hours.

TABLE 11

DEMONSTRATION OF SUBSTANTIVITY

| Sample | Viscosity (cps) | Observations Initially after sample pipetted onto VITRO-SKIN | Observations after 1 minute | Observations after 1.5 hours |
|---|---|---|---|---|
| C4 | 18 | Sample flows over the entire surface of the VITRO-SKIN and runs off of the edge onto the bottom of the jar | No sample remaining on the VITRO-SKIN Not Substantive | No sample remaining on the VITRO-SKIN Not Substantive |
| Water | 0 | Sample does not wet the VITRO-SKIN well and runs off the edge onto the bottom of the jar | No sample remaining on the VITRO-SKIN Not Substantive | No sample remaining on the VITRO-SKIN Not Substantive |
| 10% Ex4 | 11.3 | Sample does not completely wet VITRO-SKIN and the majority runs off the edge onto the bottom of the jar. The amount of sample remaining on (wetting) the | No sample remaining on the VITRO-SKIN Not Substantive | No sample remaining on the VITRO-SKIN Not Substantive |

TABLE 11-continued

DEMONSTRATION OF SUBSTANTIVITY

| Sample | Viscosity (cps) | Observations Initially after sample pipetted onto VITRO-SKIN | Observations after 1 minute | Observations after 1.5 hours |
|---|---|---|---|---|
| | | VITRO-SKIN is more than observed for the Water sample. | | |
| 15% Ex4 | 16.6 | Sample does not completely wet VITRO-SKIN and the majority runs off the edge onto the bottom of the jar. The amount of sample remaining on (wetting) the VITRO-SKIN is more than observed for the 10% Ex4 sample. | No sample remaining on the VITRO-SKIN Not Substantive | No sample remaining on the VITRO-SKIN Not Substantive |
| 25% Ex4 | 113 | Sample wets VITRO-SKIN and the majority remains in contact with VITRO-SKIN. Some runs off the edge onto the bottom of the jar. The amount of sample remaining on (wetting) the VITRO-SKIN is more than observed for the 15% Ex4 sample. | A thin layer of light brown to yellow sample over half of the area of the VITRO-SKIN is observed. Substantive | No sample remaining on the VITRO-SKIN Not Substantive |
| 33% Ex4 | 300 | Sample wets VITRO-SKIN and the majority remains in contact with VITRO-SKIN. Some runs off the edge onto the bottom of the jar. The amount of sample remaining on (wetting) the VITRO-SKIN is more than observed for the 25% Ex4 sample | A dark brown/red layer is observed over 90% of the VITRO-SKIN. Substantive | No sample remaining on the VITRO-SKIN Not Substantive |
| 50% Ex4 | 1,734 | Sample forms a large pool on VITRO-SKIN and nearly the entire sample remains in contact with VITRO-SKIN. Very little runs off the edge onto the bottom of the jar. The amount of sample remaining on (wetting) the VITRO-SKIN is more than observed for the 33% Ex4 sample | A dark brown/red layer, thicker than that observed for the 33% Ex4 sample, covers 80% of the VITRO-SKIN. It appears that the original pool is still intact. Substantive | No sample remaining on the VITRO-SKIN Not Substantive |
| Ex4 | 77,000 | Sample forms a large pool on VITRO-SKIN and the entire sample remains in contact with VITRO-SKIN. None runs off the edge onto the bottom of the jar. The entire square is not coated because the moisturizer sample is pooled in the center. | A dark brown/red layer, thicker than that observed for the 50% Ex4 sample, covers 80% of the VITRO-SKIN. It appears that the original pool is still intact. Substantive | A thin red/brown layer covering ~75% VITRO-SKIN is observed. It appears to be in the same location/area as the original pool of sample. Substantive |

Test Method—Evaluation Precipitate Formation

It is thought that some excipients (inactives) may form a CHG complex, which is visible as a precipitate. Thus, CHG which complexes with an excipient, forming a precipitate would not be available for antimicrobial efficacy. The purpose of the precipitation formation testing was to observe the potential of an excipient to form a precipitates with CHG under the following test conditions.

A solution containing 3.72% (w/w) CHG was prepared by diluting 18.6% w/w CHG stock solution with water. Sample excipient solutions were prepared with distilled water to various concentrations of excipients according to Tables 12-16, below. The pH of the solutions was then adjusted to both a low pH and a high pH using either gluconic acid or NaOH. Then 6 mL of each pH adjusted excipient sample solution was transferred into a separate vial and an equal amount (6 mL) of 3.72% CHG was added to form a 1:1 mixture (12 mL total). After combining the CHG solution with the excipient solution, the vial of the mixture was briefly swirled to mix. The mixtures were visually assessed for the presence/formation of a precipitate within 30 minutes. The results are shown in Tables P1-P5, where "Y" means precipitate was observed; "N" means no precipitate was observed; "*1" means the mixture could not be tested because a gel-like mass was formed when adding gluconic acid to reduce the pH down; and "*2" means the mixture could not be tested because it started to thicken when adding NaOH to raise the pH. For all the samples evaluated for formation of precipitate the weight percent of CHG was 3.72%, this equated to 0.22 grams CHG. Since CHG has a molecular weight of 897.8; each sample had 0.245 mMol CHG, which is 0.123 milliequivalents of CHG.

TABLE 12

|  | P1 | P2 | P3 | P4 | P5 | P6 |
|---|---|---|---|---|---|---|
| Inactive | Sodium Saccharin | Sodium Saccharin | Sodium Saccharin | Potassium Sorbate | Potassium Sorbate | Potassium Sorbate |
| Inactive wt % | 2.00 | 1.00 | 0.50 | 2.00 | 1.00 | 0.50 |
| Inactive (grams) | 0.12 | 0.06 | 0.03 | 0.12 | 0.06 | 0.03 |
| Low pH | 3.98 | 4.00 | 3.95 | 5.40 | 5.09 | 4.65 |
| Precipitation at Low pH | Y | Y | Y | *1 | *1 | *1 |
| High pH | 6.94 | 6.90 | 7.05 | 6.91 | 6.71 | 6.95 |
| Precipitation at High pH | Y | Y | Y | Y | Y | Y |

TABLE 13

|  | P7 | P8 | P9 | P10 | P11 | P12 |
|---|---|---|---|---|---|---|
| Inactive | Sodium Benzoate | Sodium Benzoate | Sodium Benzoate | KCL | KCL | KCL |
| Inactive wt % | 2.00 | 1.00 | 0.50 | 2.00 | 1.00 | 0.50 |
| Inactive (grams) | 0.12 | 0.06 | 0.03 | 0.12 | 0.06 | 0.03 |
| Low pH | 5.22 | 4.74 | 4.50 | 3.84 | 3.80 | 4.12 |
| Precipitation at Low pH | Y | Y | Y | Y | Y | N |
| High pH | 7.07 | 7.11 | 7.18 | 7.10 | 7.21 | 7.09 |
| Precipitation at High pH | Y | Y | Y | Y | Y | N |

TABLE 14

|  | P13 | P14 | P15 | P16 | P17 | P18 |
|---|---|---|---|---|---|---|
| Inactive | NaCl | NaCl | NaCl | $H_3PO_4$ | $H_3PO_4$ | $H_3PO_4$ |
| Inactive wt % | 2.00 | 1.00 | 0.50 | 2.00 | 1.00 | 0.50 |
| Inactive (grams) | 0.12 | 0.06 | 0.03 | 0.12 | 0.06 | 0.03 |
| Low pH | 4.04 | 3.90 | 4.13 | 4.25 | 4.12 | 4.21 |
| Precipitation at Low pH | Y | Y | Y | Y | Y | Y |
| High pH | 6.94 | 6.90 | 6.95 | 6.92 | 6.95 | 6.76 |
| Precipitation at High pH | Y | Y | Y | Y | Y | Y |

TABLE 15

|  | P19 | P20 | P21 | P22 | P23 | P24 |
|---|---|---|---|---|---|---|
| Inactive | Citric Acid | Citric Acid | Citric Acid | NaCMC (cellulose gum) | NaCMC (cellulose gum) | NaCMC (cellulose gum) |
| Inactive wt % | 2.00 | 1.00 | 0.50 | 2.00 | 1.00 | 0.50 |
| Inactive (grams) | 0.12 | 0.06 | 0.03 | 0.12 | 0.06 | 0.03 |
| Low pH | 4.00 | 4.18 | 3.98 | 4.31 | 4.24 | 4.23 |
| Precipitation at Low pH | Y | Y | Y | Y | Y | Y |
| High pH | 6.95 | 6.96 | 7.04 | 7.04 | 6.96 | 7.36 |
| Precipitation at High pH | Y | Y | Y | Y | Y | Y |

TABLE 16

|  | P25 | P26 | P27 | P28 | P29 | P30 |
|---|---|---|---|---|---|---|
| Inactive | Carbomer 954 | Carbomer 954 | Carbomer 954 | Glyceryl Polymethacrylate | Glyceryl Polymethacrylate | Glyceryl Polymethacrylate |
| Inactive wt % | 2.00 | 1.00 | 0.50 | 2.00 | 1.00 | 0.50 |
| Inactive (grams) | 0.12 | 0.06 | 0.03 | 0.12 | 0.06 | 0.03 |
| Low pH | *2 | *2 | 3.82 | 3.93 | 4.04 | 3.94 |
| Precipitation at Low pH | *2 | *2 | Y | Y | Y | Y |
| High pH | *2 | *2 | *2 | 7.28 | 7.07 | 7.16 |
| Precipitation at High pH | *2 | *2 | *2 | Y | Y | Y |

TABLE 17

|  | P31 | P32 | P33 | P34 | P35 |
|---|---|---|---|---|---|
| Inactive | Hydroxypropyl Guar Jaguar HP-60 | HEC Natrosol 250H | *Aloe Vera* gel | Xanthan gum | HPMC |
| Inactive wt % | 1.0 | 1.0 | 1.0 | 1.6 | 0.5 |
| Low pH | 3.7 | 4.08 | 3.96 | 4.47 | 3.93 |
| Precipitation at Low pH | N | N | N | N | N |
| High pH | 7.9 | 6.75 | 7.02 | 7.27 | 7.23 |
| Precipitation at High pH | N | N | N | N | N |

Sample Preparation for:
Test Method B2—Second Antimicrobial Efficacy Testing
Test Method C2—Second % Recovery of CHG by HPLC Analysis Additional samples were prepared to be assayed by HPLC and by Antimicrobial Efficacy. These additional samples were selected to represent some of the excipients which also caused precipitation, according to the results shown in Tables 12-16. The excipients (inactives) chosen for this experiment included Carbomer, NaCMC, sodium saccharin, glyceryl polymethacrylate. These excipients (inactives) were prepared as 0.5% wt/wt solutions and were adjusted to the pH values indicated in the table below. A 0.22% wt/wt solution of CHG was prepared at a pH of 6. All pH adjustments were made using either gluconic acid or sodium hydroxide. Each of the above excipient solutions (5 mL) were mixed with an equal amount (5 mL) of CHG solution (0.22% wt/wt). The mixtures were allowed to stand for 15 minutes at ambient conditions, along with a control CHG solution. All of these samples were centrifuged at 14,000 g for 15 minutes. After centrifugation, supernatant was carefully transferred to a new vial and submitted for Antimicrobial Efficacy testing (TEST METHOD B2) and HPLC testing (TEST METHOD C2), see below.

Test Method B2—Second Antimicrobial Efficacy Testing

For Test Method B2 the above Test Method B was followed, with the following changes:
1. Bacteria was MRSA (methicillin-resistant *Staphylococcus aureus*), ATCC 33592, instead of *P. aeruginosa*.
2. Inoculum level was approximately 6.2 logs, instead of 5.8 logs.
3. Incubation time with MRSA was 4 minutes, instead of 2.5 minutes.
4. Neutralizer was Neutralizing Buffer, instead of D/E Neutralizing Broth.
5. Incubation of the Petrifilm plates was 38 hours, instead of 43 hours.

HPLC Test Method C2—Second % Recovery of CHG by HPLC Analysis

HPLC analysis was performed to approximate the amount of available CHG, not "inhibited" by the moisturizer. Reverse phase gradient HPLC analysis of the provided solutions/suspensions were performed using an Agilent 1100 system consisting of a binary pump, 100-position autosampler, heated column compartment and diode array absorbance detector (DAD). Separations were performed under the following chromatographic conditions. The sample injection volume was 0.5 uL. The HPLC column used was an Agilent Zorbax 4.6×75 mm, 3.5 μm SB-C18 column. The column temperature was maintained at 40° C. The flow rate was 0.5 mL/min. The mobile phase consisted of 2 solvent mixtures: solvent A=100% water+0.1% v/v TFA and Solvent B=100% Methanol+0.1% v/v TFA. A programmed linear gradient mobile phase was used: 70/30 Solvent A/Solvent B (2 minute hold) to 100% B (2 minute hold) over 15 minutes (linear). Step back to initial conditions, 5 minute re-equilibration. Elution time for chlorhexidine was approximately 12.7 minutes. Detection was by UV-VIS at 260 nm (reference=550 nm). A percent recovery value was calculated for each inhibitory agent (IA) by ratioing the integrated peak area for the IA with the integrated peak area for the control sample*100 (i.e. [(Integrated peak area IA/Integrated peak area control)*100]). The percent recovery of CHG results are reported in table 18, below.

TABLE 18

| Sample | Excipient (Inactive) wt % | CHG wt % | pH | Log Reduction of MRSA | HPLC % Recovery CHG |
|---|---|---|---|---|---|
| CHG Control | 0.0 | 0.22 | — | 3.0 | 100.0 |
| Carbomer 954 | 0.50 | 0.22 | 5.82 | 0.0 | 15.6 |
| Glyceryl Polymethacrylate | 0.50 | 0.22 | 5.89 | 1.9 | 90.2 |
| NaCMC (cellulose gum) | 0.50 | 0.22 | 6.04 | 0.5 | 38.0 |
| Sodium Saccharin | 0.50 | 0.22 | 6.04 | 0.0 | 0.1 |

Additional ANTIMICROBIAL EFFICACY testing was done on Example 4 according to the following test method.

Test Method B3—Antimicrobial Efficacy Testing

Test Organism for Antimicrobial Efficacy Test Method B3

The test organism for this assay was *Pseudomonas aeruginosa* (ATCC 27853). The initial suspension was prepared by suspending bacterial colonies from overnight growth on Sheep Blood Agar in 0.3 mM phosphate-buffered water (PBW). The stock PBW (0.25M) was prepared as follows: To 500 ml deionized water was added 34 g potassium dihydrogen phosphate. The pH was adjusted to 7.2 using 10N sodium hydroxide. The contents were diluted to 1 liter using deionized water. This was filter sterilized. Then 0.62 microLiters of stock solution were added to 500 mL DI water making a 0.3 mM PBW solution. A 0.5 McFarland turbidity standard was used to obtain a cell density of approximately $1.5 \times 10^8$ CFU/mL. The suspension was enumerated at the beginning of the test period.

Inoculum Preparation for Antimicrobial Efficacy Test B3

The inoculum was prepared by diluting the initial suspension 10-fold in PBW. Each test sample was inoculated with approximately 5.5 logs bacteria.

Neutralizing Broth: D/E Neutralizing Broth was purchased as a solid and reconstituted according to directions from Difco Laboratories, Detroit Mich.

Test Materials for Antimicrobial Efficacy Test B3

The test mixture was prepared at a ratio of 1 mL PERIDEX plus 1 g moisturizer Example 4, plus 0.5 mL phosphate buffered water (PBW) and mixed by vortexing. The mixture was incubated at ambient temperature for 5 minutes prior to inoculation. The controls for the testing were 1 mL of PBW (for direct enumeration of inoculum) and 1 mL PERIDEX.

Test Method B3—Measurement of Antimicrobial Activity:

The mixture and controls were inoculated with forty microliters of bacterial inoculum per mL, and vortexed for 20 seconds. After 5 minutes at ambient temperature, 1 mL of the inoculated test mixture or controls were added to 20 mL D/E Neutralizing Broth and vortexed.

Dilutions were prepared in PBW, and 1 mL, in duplicate, was pipetted into Aerobic Count Petrifilm Plates, 3M Company. All plates were incubated at 37° C. for 48 hours.

Plates were counted with the 3M Petrifilm Plate Reader, and confirmed manually.

Colony Forming Units (CFU) were recorded, duplicate plates averaged and multiplied by the dilution factor for CFU/mL, and multiplied by the total test volume after neutralization (21 mL) for the CFU/test sample. Log 10 CFU/test of multiple tests were averaged and the log 10 reduction was calculated from the mean PBW control. The log 10 reduction of *Pseudomonas* for the test mixture of 1:1:0.5 (Peridex:3M moisturizer:PBW) was 4.4 log units. The log 10 reduction of *Pseudomonas* for the Control mixture of 1:1:0.5 (Peridex: PBW:PBW) was 4.5 log units.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of moisturizing while decolonizing mammalian tissue, the method comprising:
    applying a multi-valent cationic antiseptic composition to oral tissue, wherein the multivalent cationic antiseptic persists on oral tissue for up to 5 hours, and
    applying a moisturizer composition to at least a portion of the oral tissue; wherein the moisturizer composition is applied 4 hours or less before or 4 hours or less after applying the multi-valent cationic antiseptic composition;
    wherein the moisturizer composition essentially excludes any component which causes a precipitate when combined with a multi-valent cationic antiseptic used in the multi-valent cationic antiseptic composition when tested according to Test Method F;
    wherein the multi-valent cationic antiseptic is other than a metal ion; and
    wherein the essentially excluded component is selected from the group consisting of polyanions of polycarboxylates, polysulfonates, polysulfates, and organic and inorganic polyphosphates; anions of alkylsulfates, arylsulfates, alkylsulfonates, arylsulfonates, alkylcarboxylates, arylcarboxylates, alkylphosphates, arylphosphates; halide salts; and combinations thereof, wherein the alkyl groups have a chain length of greater than 6 carbon atoms and the aryl groups have 6 or more carbon atoms, and wherein the essentially excluded component is not present or present at a concentration less than 0.1 percent by weight of the composition, except halide salts which are not present or present at a concentration not greater than 0.2 wt-% by weight of the composition.

2. The method of claim 1, wherein the moisturizer composition is such that a log reduction in the number of viable bacterial cells of at least 2 is provided when $10^6$ cfu of *Pseudomonas aeruginosa* (ATCC 27853) are combined with a mixture of 1.1 g of the moisturizer composition and 1.5 g of a multi-valent cationic antiseptic composition containing 0.12 weight percent of the multi-valent cationic antiseptic according to Test Method B.

3. A method of moisturizing while decolonizing mammalian tissue, the method comprising:
    applying a multi-valent cationic antiseptic to the tissue wherein the multivalent cationic antiseptic persists on the tissue for up to 5 hours, and
    applying a substantive moisturizer composition to at least a portion of the same tissue; wherein the moisturizer composition is applied 4 hours or less before or 4 hours or less after applying the multi-valent cationic antiseptic;
    wherein the mammalian tissue is oral tissue of a subject;
    wherein the multi-valent cationic antiseptic is other than a metal ion;
    wherein the substantive moisturizer composition is such that a log reduction in the number of viable bacterial cells of at least 2 is provided when $10^6$ cfu of *Pseudomonas aeruginosa* (ATCC 27853) are combined with a mixture of 1.1 g of the substantive moisturizer composition and 1.5 g of a multi-valent cationic antiseptic composition containing 0.12 weight percent of the multi-valent cationic antiseptic according to Test Method B; and
    wherein the substantive moisturizer composition essentially excludes a component selected from the group consisting of polyanions of polycarboxylates, polysulfonates, polysulfates, and polyphosphates; chelators; inorganic buffers; anions of alkylsulfates, arylsulfates, alkylsulfonates, arylsulfonates, alkylcarboxylates, arylcarboxylates, alkylphosphates, arylphosphates; and combinations thereof; wherein the alkyl groups have a chain length of greater than four carbon atoms, and the aryl groups include at least 6 carbon atoms.

4. The method of claim 1, wherein the moisturizer composition has a pH of 3 to 8.

5. The method of claim 1, wherein the moisturizer composition has a viscosity of at least 50 centipoise.

6. The method of claim 1, wherein the multi-valent cationic antiseptic is selected from the group consisting of biguanides, bisbiguanides, polybiguanides, polymeric quaternary ammonium compounds, and combinations thereof.

7. The method of claim 6, wherein the multi-valent cationic antiseptic is a chlorhexidine salt.

8. The method of claim 1, wherein the multi-valent cationic antiseptic is included in a composition further comprising a sweetener selected from the group consisting of sucralose, aspartame, xylose, sucrose, maltose, mannose, glucose, xylitol, sorbitol, mannitol, erythritol, maltitol, lactitol, and a combination thereof.

9. The method of claim 1, wherein the moisturizer composition has a shrinkage of less than 10 percent when dried under ambient conditions for 2 hours and/or wherein the moisturizer composition when dried on a surface under ambient conditions does not form a self supporting film.

10. The method of claim 1, further comprising applying a de-briding composition comprising hydrogen peroxide.

11. The method of claim 10, wherein the hydrogen peroxide is stabilized with a component which maintains the de-briding composition at a pH of 2.5 to 4, and wherein the de-briding composition essentially excludes any component which causes a precipitate when combined with a multi-valent cationic antiseptic used in the multi-valent cationic antiseptic composition when tested according to Test Method F.

12. A method of moisturizing oral tissue of a patient requiring intubation, the method comprising:
    applying a moisturizer composition to at least a portion of the oral-tissue, an endotracheal tube, or both;
    inserting an endotracheal tube through the patients oral cavity and into the patient's trachea;
    wherein the endotracheal tube is coated or impregnated with a cationic antiseptic;
    wherein the moisturizer composition is applied 4 hours or less after inserting said tube;
    wherein the moisturizer composition essentially excludes any component which causes a precipitate when combined with the cationic antiseptic when tested according to Test Method F;
    wherein the essentially excluded component is selected from the group consisting of polyanions of polycarbox, lapolysulfonates, polysulfates, and organic and inorganic polyphosphates; anions of alkylsulfates, arylsulfates, alkylsulfonates, arylsulfonates, alkylcarboxylates, arylcarboxylates, alkylphosphates, arylphosphates; halide salts; and combinations thereof, wherein the alkyl groups have a chain length of greater than 6 carbon atoms and the aryl groups have 6 or more carbon atoms, and wherein the essentially excluded component is not present or present at a concentration less than 0.1 percent by weight of the composition, except halide salts which are not present or present at a concentration not greater than 0.2 wt-% by weight of the composition; and wherein the cationic antiseptic is other than a metal ion.

13. The method of claim 1, wherein the moisturizer composition is applied in at least one additional application.

14. The method of claim 3, wherein the substantive moisturizer composition is applied in at least one additional application.

15. The method of claim 12, wherein the substantive moisturizer composition is applied to the oral tissue in at least one additional application.

16. The method of claim 1, wherein the essentially excluded component is further selected from the group consisting of sodium saccharin, potassium sorbate, sodium benzoate, potassium chloride, sodium chloride, phosphoric acid, citric acid, sodium carboxymethylcellulose, carbomers, and glyceryl polymethacrylate.

17. The method of claim 3, wherein the essentially excluded component is further selected from the group consisting of sodium saccharin, potassium sorbate, sodium benzoate, potassium chloride, sodium chloride, phosphoric acid, citric acid, sodium carboxymethylcellulose, carbomers, and glyceryl polymethacrylate.

18. The method of claim 12, wherein the essentially excluded component is further selected from the group consisting of sodium saccharin, potassium sorbate, sodium benzoate, potassium chloride, sodium chloride, phosphoric acid, citric acid, sodium carboxymethylcellulose, carbomers, and glyceryl polymethacrylate.

* * * * *

UNITED STATES PATENT AND TRADEMARK OFFICE
CERTIFICATE OF CORRECTION

PATENT NO. : 8,460,689 B2
APPLICATION NO. : 12/775197
DATED : June 11, 2013
INVENTOR(S) : Katie Wlaschin et al.

It is certified that error appears in the above-identified patent and that said Letters Patent is hereby corrected as shown below:

In the Specification

Column 10
Line 40, delete "auerginosa" and insert -- aeruginosa --, therefor.

Column 11
Line 36, delete "may by" and insert -- may be --, therefor.

Column 13
Line 5, delete "Esherichia" and insert -- Escherichia --, therefor.
Line 42, delete "phenlyene," and insert -- phenylene, --, therefor.

Column 14
Line 21, delete "like" and insert -- like. --, therefor.
Line 32, delete "bacteriacidal" and insert -- bactericidal --, therefor.
Line 35, delete "polybiquanide." and insert -- polybiguanide. --, therefor.

Column 15
Line 2, delete "pentraerythritol," and insert -- pentaerythritol, --, therefor
Line 2, delete "panetothenol," and insert -- pantothenol, --, therefor.

Column 18
Line 56, delete "Crodaphos" and insert -- Crodafos --, therefor.

Column 21
Line 43, delete "cleaning" and insert -- cleaning. --, therefor.

Column 22
Line 36, delete "thereof" and insert -- thereof. --, therefor.

Signed and Sealed this
Ninth Day of December, 2014

Michelle K. Lee
*Deputy Director of the United States Patent and Trademark Office*

Colum 25
Line 42, delete "Psuedomonas" and insert -- Pseudomonas --, therefor.

Column 32
Line 49, delete "isoparafins" and insert -- isoparaffins --, therefor.
Line 53, delete "isoparafins," and insert -- isoparaffins, --, therefor.

Column 33
Line 44, delete "non-steorodial" and insert -- non-steroidal --, therefor.

Column 34
Line 5, delete "clortimazole," and insert -- clotrimazole, --, therefor.
Line 6, delete "metronizazole," and insert -- metronidazole, --, therefor.
Line 8, delete "polymixin," and insert -- polymyxin, --, therefor.
Line 48, delete "polyamid" and insert -- polyamide --, therefor.
Line 65, delete "benzalkoium" and insert -- benzalkonium --, therefor.

Column 35
Line 17, delete "the a" and insert -- the --, therefor.

In the Claims

Column 60
Lines 60-61, claim 12, delete "polycarbox, lapolysulfonates," and insert -- polycarboxylates, polysulfonates, --, therefor.